United States Patent [19]

Monkovic et al.

[11] 3,959,290

[45] *May 25, 1976

[54] 3,14-SUBSTITUTED-8-OXAMORPHINANS

[75] Inventors: Ivo Monkovic, Candiac; Yvon Lambert, Brossard, both of Canada

[73] Assignee: Bristol-Myers Company, New York, N.Y.

[ * ] Notice: The portion of the term of this patent subsequent to Dec. 10, 1991, has been disclaimed.

[22] Filed: Nov. 27, 1974

[21] Appl. No.: 527,667

Related U.S. Application Data

[63] Continuation-in-part of Ser. No. 380,515, July 18, 1973, Pat. No. 3,853,889.

[52] U.S. Cl. .......... 260/293.55
[51] Int. Cl.[2] .......... C07D 491/04
[58] Field of Search .......... 260/293.55

[56] References Cited

UNITED STATES PATENTS

| | | | |
|---|---|---|---|
| 3,476,757 | 11/1969 | Cross | 260/268 |
| 3,480,638 | 11/1969 | Block et al. | 260/294.3 |
| 3,632,591 | 1/1972 | Albertson et al. | 260/293.54 |
| 3,639,407 | 2/1972 | Clarke et al. | 260/293.54 |
| 3,700,734 | 10/1972 | Robinson et al. | 260/293.54 |
| 3,732,233 | 5/1973 | Pars et al. | 260/293.55 |
| 3,764,606 | 10/1973 | Akkerman et al. | 260/293.54 |
| 3,853,889 | 12/1974 | Monkovic et al. | 260/293.55 |

OTHER PUBLICATIONS

Chignell et al., J. Med. Chem. 1965, vol. 8, pp. 235–238.

Eddy et al., synthetic Analgesics vol. 8, Part IIB, 6,7-Benzomorphans, pp. 115–182, N.Y., Pergamon Press, 1966.

May et al., J. Org. Chem., 1961, vol. 26, pp. 188–193.

May et al., J. Org. Chem., 1961, vol. 26, pp. 1621–1624.

Kugita et al., J. Org. Chem. 1961, Vol. 26, pp. 1954–1957.

Murphy et al., J. Org. Chem. 1960, Vol. 25, pp. 1386–1388.

Saito et al., J. Org. Chem., 1961, vol. 26, pp. 4536–4540.

Hellerbach et al., Synthetic Analgesics, vol. 8, Part IIA Morphinans, pp. 3–70, N.Y., Pergamon, 1966.

*Primary Examiner*—Natalie Trousof
*Attorney, Agent, or Firm*—Robert E. Havranek

[57] ABSTRACT

N-Substituted-3-hydroxy-8-cxamorphinans have been found to possess potent narcotic agonist and/or antagonist activity. In particular, the compound 1-N-cyclopropylmethyl-3-hydroxy-14β-methyl-8-oxamorphinan has been found to possess potent narcotic antagonist and agonist activity. These compounds are prepared by total synthesis and are not derived from opium alkaloids.

5 Claims, No Drawings

3,14-SUBSTITUTED-8-OXAMORPHINANS

CROSS-REFERENCES TO RELATED APPLICATIONS

This application is a continuation-in-part of a copending application Ser. No. 380,515, filed July 18, 1973, now U.S. Pat. No. 3,853,889.

BACKGROUND OF THE INVENTION

1. Field of the Invention:

This invention embodies new and novel compounds useful as analgesics and/or narcotic antagonists and a new and novel total synthesis for their preparation.

2. Description of the Prior Art:

A. Everette May and Hiroshi Kugita, J. Org. Chem. 26, 188 (1961) describe compounds having the formula

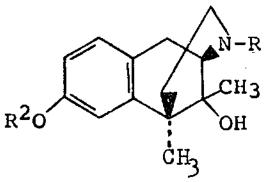

in which $R_2$ is H or methyl and R is methyl or phenethyl as being moderate to weak analgetics.

B. Everette May, James Murphy and J. Harrison Ager, J. Org. Chem. 25, 1386 (1960) report compounds having the formula

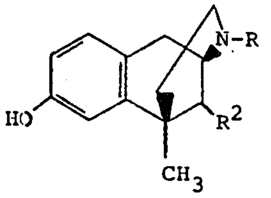

in which R is methyl or phenethyl and $R^2$ is H or methyl as being potent analgetics.

C. Everette May, Hiroshi Kugita and J. Harrison Ager, J. Org. Chem. 26, 1621 (1961) report compounds having the formula

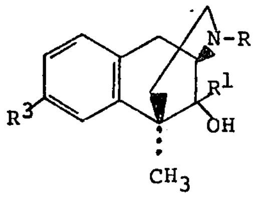

in which R is methyl or phenethyl, $R^1$ is methyl or H, $R^3$ is H, OH or methoxy as producing varying degrees of analgesia.

D. Everette May, Colin Chignell and J. Harrison Ager, J. Med. Chem. 8, 235 (1965) report compounds having the formula

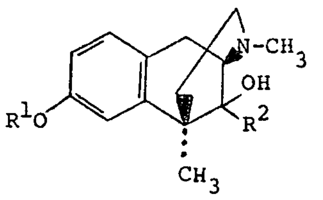

in which $R^1$ is H or methyl and $R^2$ is methyl as possessing analgetic activity.

E. Everette May and Hiroshi Kugita, J. Org. Chem. 26 1954 (1961) report the compound having the formula

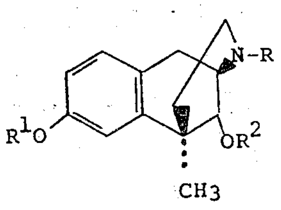

in which R is methyl or phenethyl, $R^1$ is H or methyl and $R^2$ is H or acetyl as having analgetic activity.

F. Everette May and Seiichi Sato, J. Org. Chem. 26, 4536 (1961) report compounds having the formula

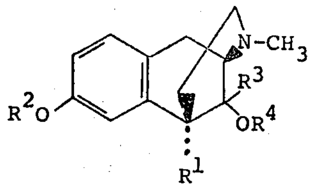

in which $R^2$ is H or methyl, $R^1$ is methyl or ethyl, $R^3$ is methyl or ethyl and $R^4$ is H or acetyl as possessing analgetic activity.

G. N. B. Eddy and E. L. May published a review of 6,7-benzomorphans in Synthetic Analgetics, Pergamon Press (1966).

SUMMARY OF THE INVENTION

Compounds having the formula

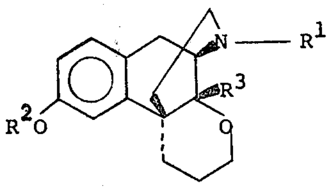

wherein $R^1$ is selected from the group comprising H, (lower)alkyl, $—CH_2—C\equiv CH$, $—CH_2—CH=CH_2$,

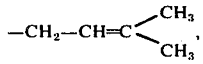,

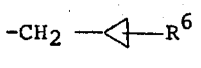, 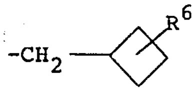, 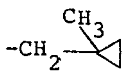,

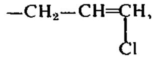,

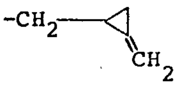 , 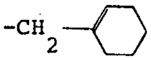 ,

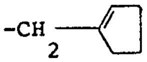

and (lower)alkenyl in which $R^6$ is H or $CH_3$, $R^2$ is selected from the group comprising H, (lower)alkyl,

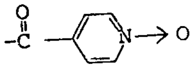

(lower)alkanoyl,

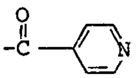 , 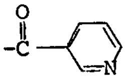

and 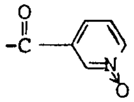 , and
$R^3$ is H or (lower)alkyl; or a pharmaceutically acceptable acid addition salt thereof are analgetic agents, narcotic antagonists or intermediates in the preparation of such agents.

DISCLOSURE OF THE INVENTION

This invention relates to the total synthesis of new and novel N-substituted-3-substituted-8-oxamorphinans having the formula

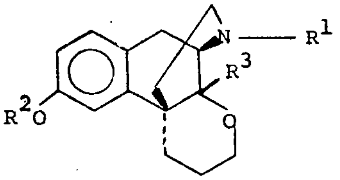

L wherein $R^1$ is selected from the group comprising H, (lower)alkyl, $—CH_2—C\equiv CH$, $—CH_2—CH=CH_2$,

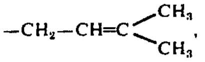

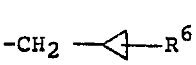 , 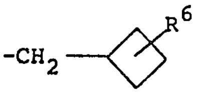 ,

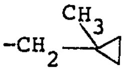 ,

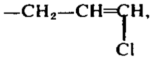

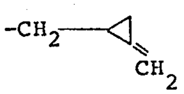 , 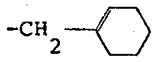 ,

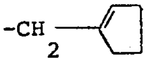 ,

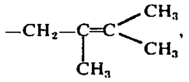 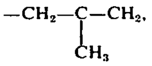

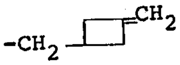 ,

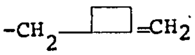 ,

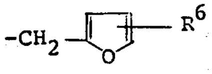 ,

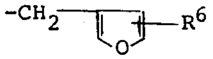 ,

, 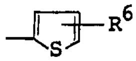 ,

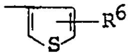 ,

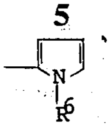

,

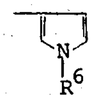

and (lower)alkenyl in which $R^6$ is H or $CH_3$, $R^2$ is selected from the group comprising H, (lower)alkyl,

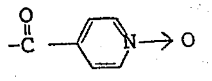

, (lower)alkanoyl,

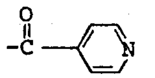

,

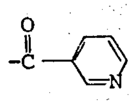

,

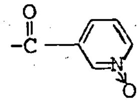

,

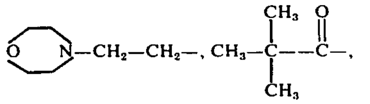

$—CH_2—O—CH_3$ ,

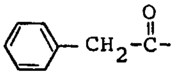

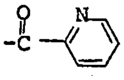

,

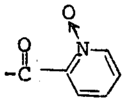

and cinnamoyl, and $R^3$ is H or (lower)alkyl; or a pharmaceutically acceptable acid addition salt thereof.

Drug abuse by thrill-seeking youth or by people looking for an escape from the realities of every day life has become more and more common place in our present society. One class of widely abused drugs are the narcotic analgetics such as codeine, morphine, meperidine, etc. It is because of the high addictive potential of these agents that much time and money are being expended by the pharmaceutical industry and by governments to try and discover and develop new non-addicting analgetics and/or narcotic antagonists.

It was therefore an object of the present invention to develop low abuse analgetics and a synthesis that would not be dependent upon opium alkaloids as starting materials and yet would be commercially feasible.

The objectives of the present invention have been achieved by the provision of the compounds of formula L and by their total synthesis from the readily available starting mmaterial 7-methoxy-3,4-dihydro-2[1H]-naphthalenone.

The compounds of the instant invention have the basic oxamorphinan nucleus which is numbered and represented by the following plane formula

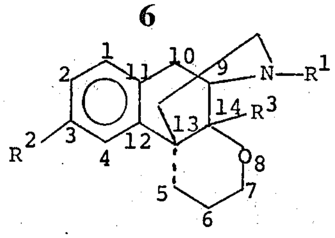

I

Although there are three asymetric carbons (asterisks) in the oxamorphinan molecule, only two diastereoisomeric (racemic) forms are possible, because the iminoethano system, attached to position 13 and 9, is geometrically constrained to a cis(1,3-diaxial)-fusion. These racemates can therefore differ only in the configuration of carbon 14. The only variable will be the cis and trans relationship of the 14 carbon substituent to the iminoethano system. When in the compounds of the present invention the 14-substituent(alkyl) is trans to the iminoethano system, we have the 14α-alkyloxaisomorphinans. When the 14-alkyl is cis to the iminoethano system, we have the 14β-alkyloxamorphinans.

The use of a graphic representation of a oxamorphinan is meant to include the dl racemic mixture and the resolved d and l isomers thereof.

The compounds of the present invention, the 14α and 14β-alkyloxamorphinans, can exist as two optical isomers, the levorotatory and dextrorotatory isomers. The optical isomers can be graphically illustrated as:

14β-alkyloxamorphinan:

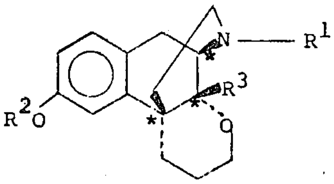

and

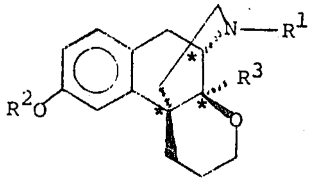

14α-alkyloxaisomorphinan:

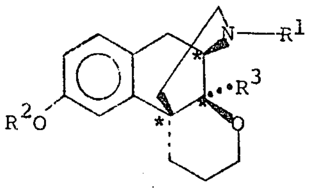

and

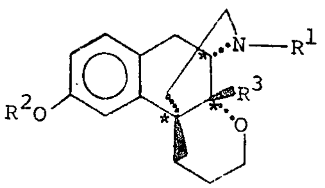

The present invention embodies all of the isomers including the optical isomers in their resolved form.

The optical isomers can be separated and isolated by fractional crystallization of the diastereoisomeric salts formed, for instance, with d- or l- tartaric acid or D-(+)-α-bromocamphor sulfonic acid. The levorotatory isomers of the compounds of the present invention are the most preferred embodiments. Other acids commonly used for resolution can be employed.

The compounds of the invention are prepared from benzomorphinans having the basic nucleus which is numbered and represented by the following plane formula

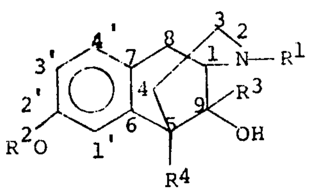

For the purpose of this disclosure, the term "(lower)" is applied to a hydrocarbon radical consisting of 1 to 6 carbon atoms, e.g., methyl, ethoxy, vinyl, ethinyl, etc. The term "(lower)alkanoyl" is an acyl radical of 2 to 6 carbon atoms, e.g., acetyl, propionyl, isobutyryl, etc. The term "pharmaceutically acceptable acid addition salt" is defined to include all those inorganic and organic acid salts of the compounds of the instant invention, which salts are commonly used to produce nontoxic salts of medicinal agents containing amine functions. Illustrative examples would be those salts formed by mixing the compounds of formula L with hydrochloric, sulfuric, nitric, phosphoric, phosphorous, hydrobromic, maleic, malic, ascorbic, citric, tartaric, pamoic, lauric, stearic, palmitic, oleic, muristic, lauryl sulfuric, napthalinesulfonic, linoleic or linolenic acid, fumaric, and the like.

The compounds of the instant invention are prepared by a total synthesis comprising multiple steps. Surprisingly, the synthesis is efficient and appears commercially feasible. The process is outlined in the following charts.

CHART I

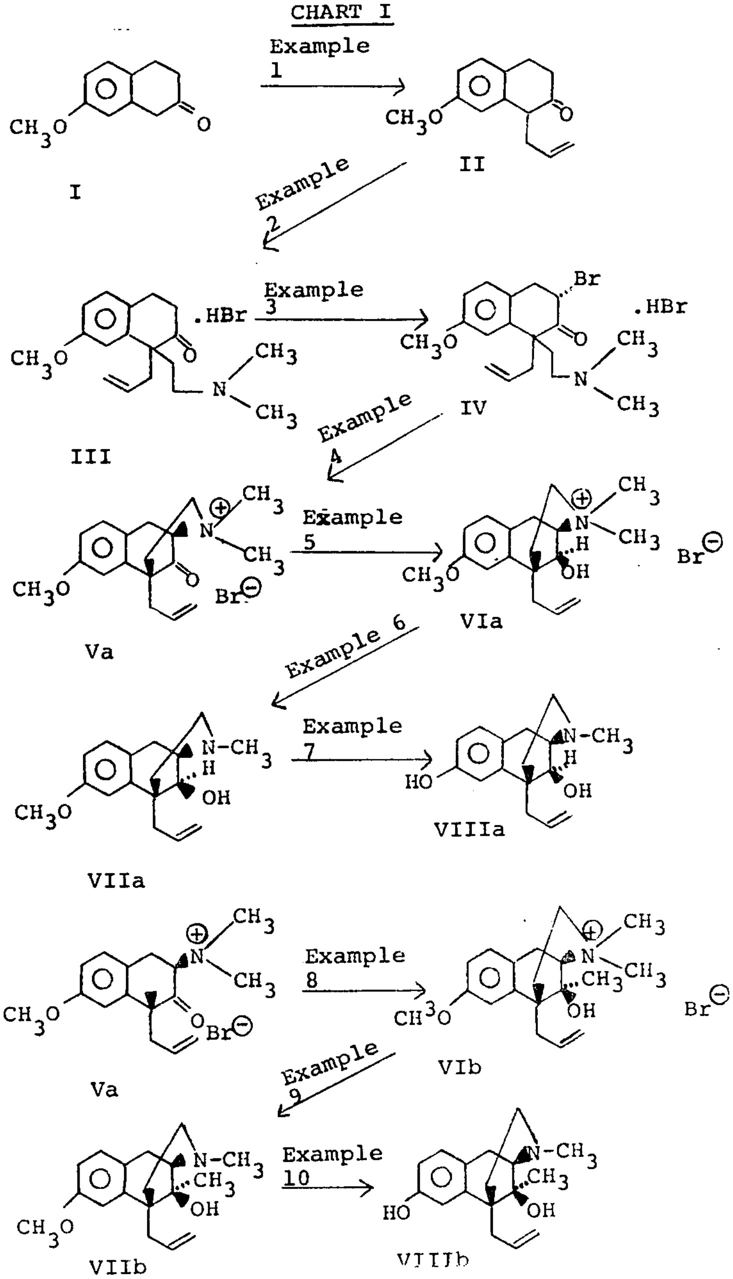

I II III IV Va VIa VIIa VIIIa Va VIb VIIb VIIIb

CHART I (con't.)
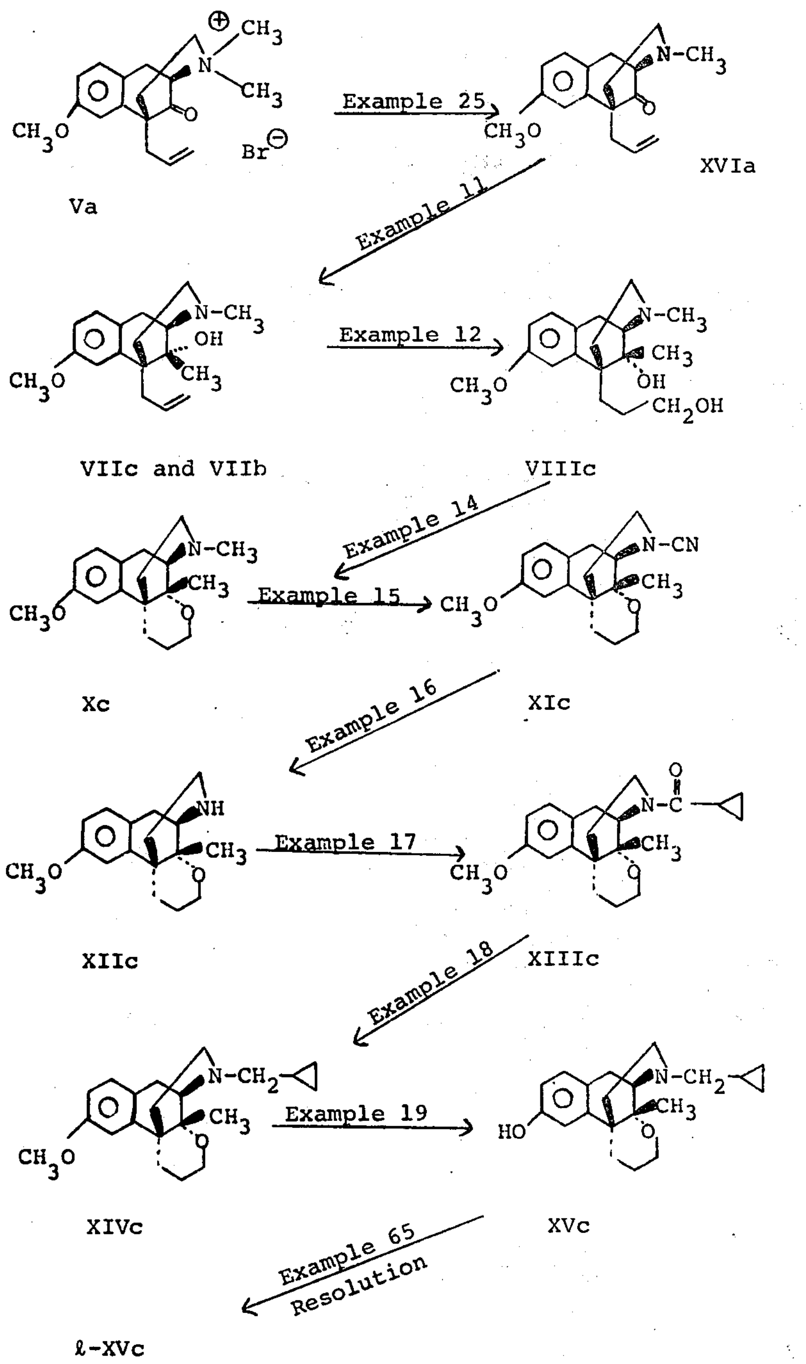
A preferred embodiment of the present invention is the compounds having the formula
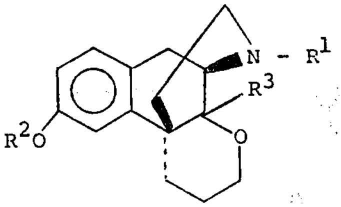
L
wherein $R^1$ is selected from the group comprising $-CH_2-C\equiv CH$, H, $-CH_2-CH=CH_2$,
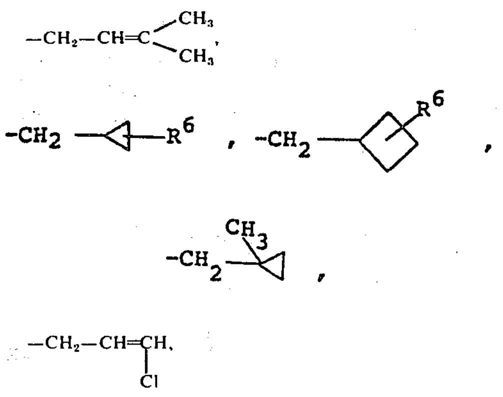

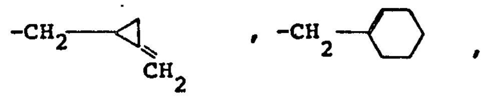

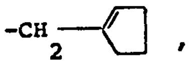

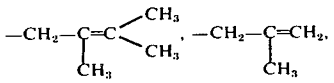

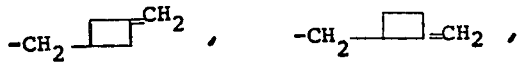

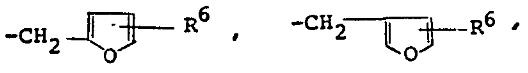

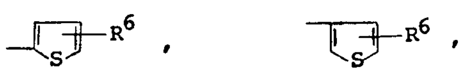

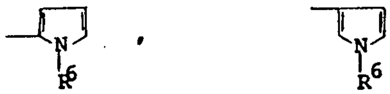

and (lower)alkenyl in which $R^6$ is H or $CH_3$, $R^2$ is selected from the group comprising H, (lower)alkyl,

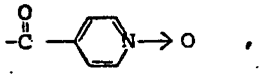

(lower)alkanoyl,

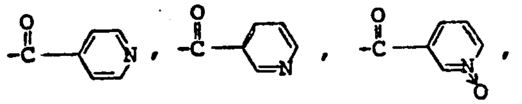

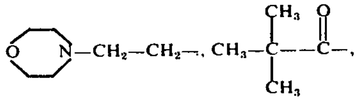

$—CH_2—O—CH_3$ ,

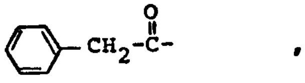

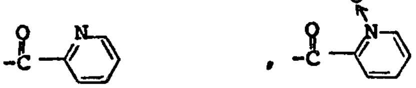

and cinnamoyl, and $R^3$ is H or (lower)alkyl; or a pharmaceutically acceptable acid addition salt thereof.

Another preferred embodiment is the compounds having the formula

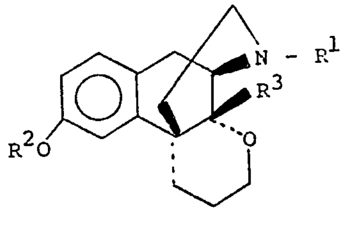

XXXX wherein $R^1$ is selected from the group comprising $—CH_2—C\equiv CH$, H, $—CH_2—CH=CH_2$,

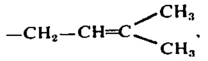

(lower) alkyl,

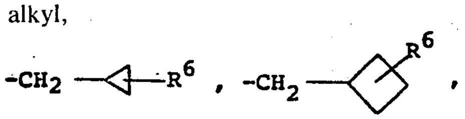

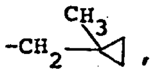

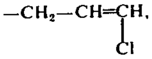

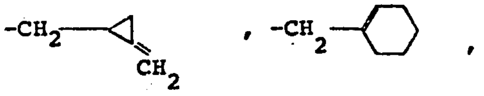

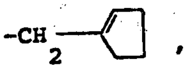

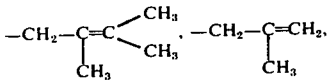

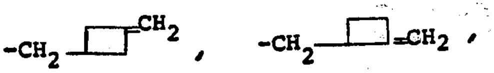

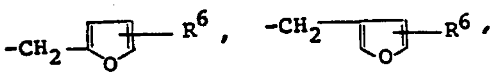

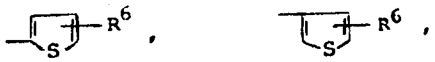

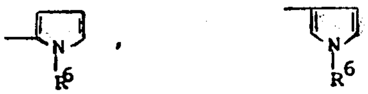

and (lower)alkenyl in which $R^6$ is H or $CH_3$, $R^2$ is selected from the group comprising H, (lower)alkyl,

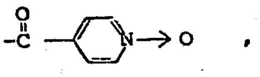

(lower)alkanoyl,

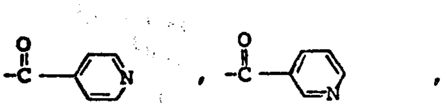

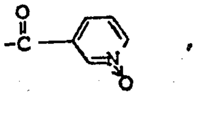

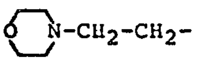 , 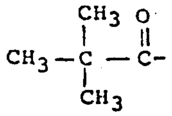 , $-CH_2-O-CH_3$ ,

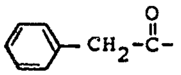 ,

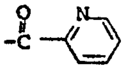 , 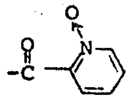

and cinnamoyl, and $R^3$ is H or (lower)alkyl; or a pharmaceutically acceptable acid addition salt thereof.

A more preferred embodiment is the compounds of the formula XXX wherein $R^1$is $-CH_2-CH{=}CH_2$, H, (lower)alkyl, $-CH_2-C\equiv CH$,

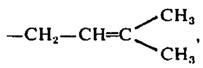

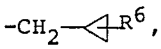

or

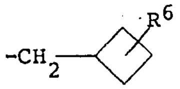

in which $R^6$ is H or $CH_3$, $R^2$ is H, $CH_3$,

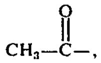

or

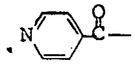

and $R^3$ is H, $CH_3$ or $C_2H_5$; or a pharmaceutically acceptable acid addition salt thereof.

Another more preferred embodiment is the compounds of formula XXXX wherein $R^1$ is

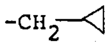

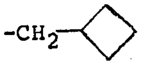

or $-CH_2-CH{=}CH_2$, $R^2$ is H, $CH_3$ or 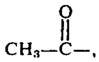

and $R^3$ is methyl; or a pharmaceutically acceptable acid, addition salt thereof.

Another preferred embodiment is the compounds having the formula

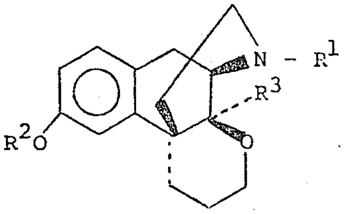

XXXXI wherein $R^1$ is selected from the group comprising $-CH_2-C\equiv CH$, $-CH_2-CH{=}CH_2$,

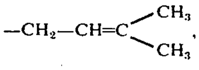

(lower)alkyl,

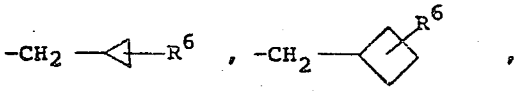

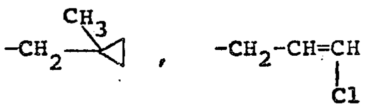

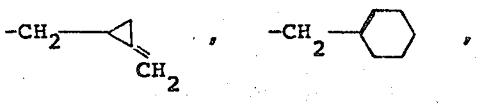

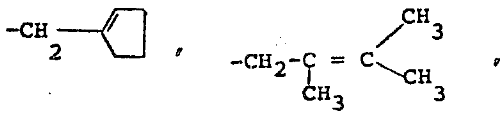

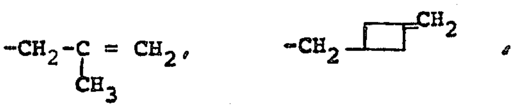

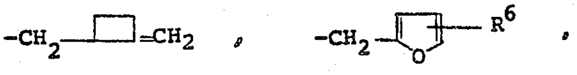

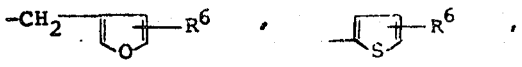

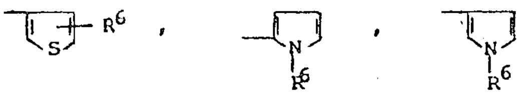

and (lower)alkenyl in which $R^6$ is H or $CH_3$, $R^2$ is selected from the group comprising H, (lower)alkyl,

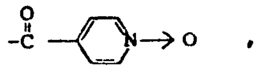

(lower)alkanoyl,

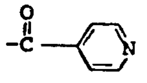 , 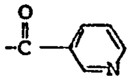 , 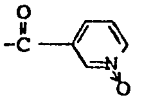 ,

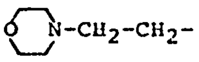 , 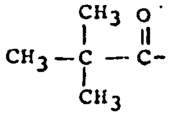 , $-CH_2-O-CH_3$ ,

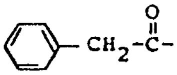 ,

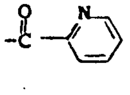 , 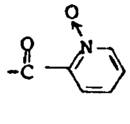

and cinnamoyl, and $R^3$ is H or (lower)alkyl; or a pharmaceutically acceptable acid addition salt thereof.

A more preferred embodiment is the compounds of the formula XXXXI wherein $R^1$ is $-CH_2-CH=CH_2$ $-CH_2-C\equiv CH$,

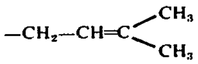

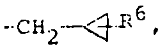 , or

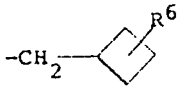

in which $R^6$ is H or $CH_3$, $R^2$ is H, $CH_3$,

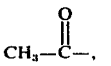

or

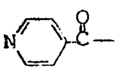 , and $R^3$ is H, $CH_3$ or $C_2H_5$; or a pharmaceutically acceptable acid addition salt thereof.

Another more preferred embodiment is the compounds of formula XXXXI wherein $R^1$ is

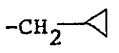 ,

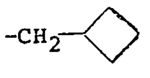 , or $-CH_2-CH=CH_2$, $R^2$ is H, $CH_3$ or 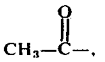

and $R^3$ is methyl; or a pharmaceutically acceptable acid addition salt thereof.

Most preferred embodiments are:

1. The compound of formula XXXX wherein $R^1$ is

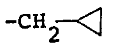 , $R^2$ is H, and $R^3$ is methyl; or the hydrochloride salt thereof.

2. The compound of formula XXXX wherein $R^1$ is

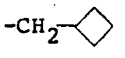 , $R^2$ is H, and $R^3$ is methyl; or the hydrochloride salt thereof.

3. The compound of formula XXXX wherein $R^1$ is $-CH_2-CH=CH_2$, $R^1$ is H, and $R^3$ is methyl; or the hydrochloride salt thereof.

4. The compound of formula XXXX wherein $R^1$ is H, $R^2$ is H or methyl; and $R^3$ is H or methyl; or an acid addition salt thereof.

5. The compound of formula XXXXI where $R^1$ is

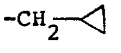 , $R^2$ is H and $R^3$ is methyl; or the hydrochloride salt thereof.

6. The compound of formula XXXXI wherein $R^1$ is

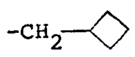 , $R^2$ is H and $R^3$ is methyl; or the hydrochloride salt thereof.

7. The compound of formula XXXXI wherein $R^1$ is $-CH_2-CH=CH_2$; $R^2$ is H and $R^3$ is methyl; or the hydrochloride salt thereof.

8. The compound of formula XXXXI wherein $R^1$ is H, $R^2$ is H or methyl and $R^3$ is H or an acid addition salt thereof.

9. The levorotatory isomers of the compound XXXX.

10. The dextrorotatory isomers of the compound XXXX.

11. The levorotatory isomers of the compound XXXXI.

12. The dextrorotatory isomers of the compound XXXXI.

13. The compound of formula XXXX wherein $R^1$ is

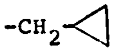 , $R^2$ and $R^3$ are hydrogen; or the hydrochloride salt thereof.

The processes for the preparation of the compounds of the instant invention are new and novel and also constitute preferred embodiments.

A preferred embodiment of the present invention is the process of preparing compounds having the formula

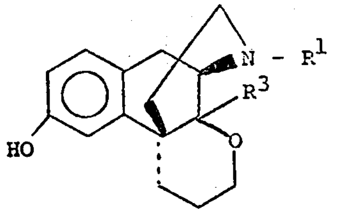

LI wherein $R^1$ is selected from the group comprising $-CH_2-C\equiv CH$, $-CH_2-CH=CH_2$,

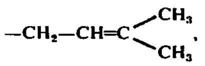

(lower)alkyl,

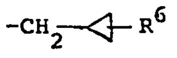 , 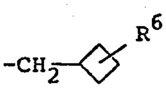 , 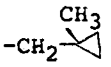 , 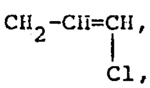

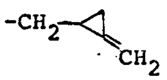 , 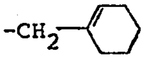 , 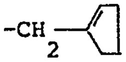 ,

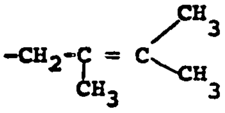 , 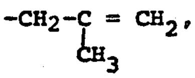

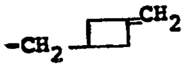 , 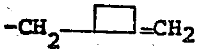 ,

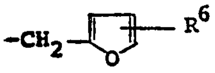 , 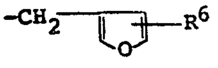 ,

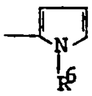 , 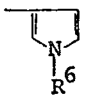 ,

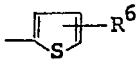 , 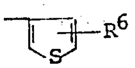 , and (lower)alkenyl in which $R^6$ is H or $CH_3$, $R^3$ is H or (lower)alkyl; which process comprises the consecutive steps of A. treating the compound having the formula

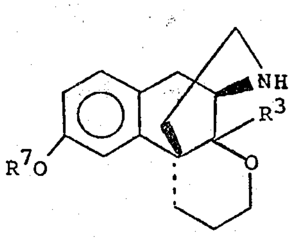

XXXXIII in which $R^7$ is (lower)alkyl and $R^3$ is as defined above, with an alkylating or acylating agent having the formula

X—(Z)—W in which W is a radical selected from the group comprising $-C\equiv CH$, $-CH=CH_2$,

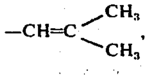

H, (lower)alkyl,

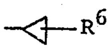 , 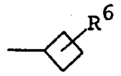 , 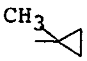 ,

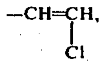

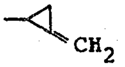 , 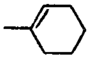 , 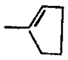 ,

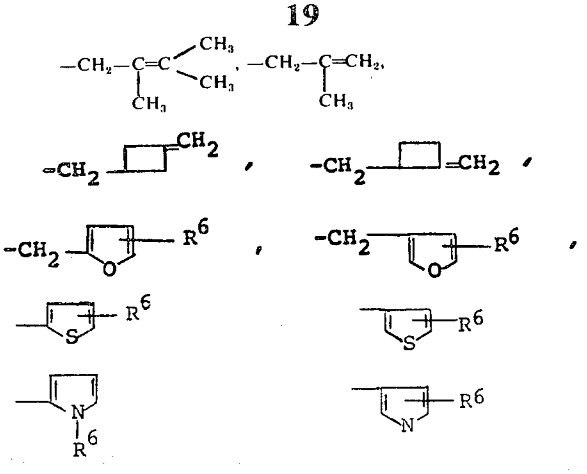

and $C_{2-6}$ alkenyl in which $R^6$ is H or $CH_3$, Z is carbonyl

or —$CH_2$— and X is chloro, bromo, or iodo, in an inert organic solvent in the presence of an appropriate base to produce the compound having the formula

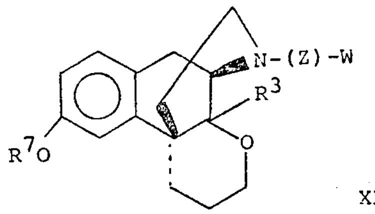

XXXXIV in which $R^3$, Z, W, and $R^7$ are as defined above; and when Z is carbonyl

B. treating compound XXXXIV with lithium aluminum hydride, in an organic solvent, to produce the compound having the formula

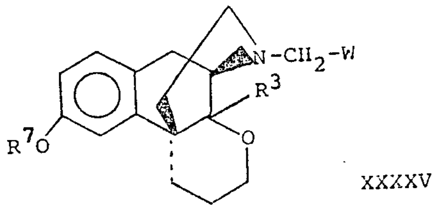

XXXXV in which $R^7$, W and $R^3$ are as defined above; and

C. cleaving the ether function of compound XXXXIV or XXXXV by treatment with an agent selected from the group comprising NaS—$C_2H_5$, hydrobromic acid, boron tribromide or pyridine hydrochloride.

For the purpose of this disclosure the term "inert organic solvent" means an organic solvent that does not participate in the reaction to the extent that it emerges unchanged from the reaction. Such solvents are methylene chloride, chloroform, dichloroethane, tetrachloromethane, benzene, toluene, ether, ethyl acetate, xylene, tetrahydrofuran, dioxane, dimethylacetamide, dimethylformamide, and the like when an acid halide is employed. When an alkylation reaction is being performed, the inert solvent used may also include (lower)alkanols such as methanol, ethanol, n-propanol, isopropanol and the like. The term "organic tertiary amine" means a tertiary amine commonly employed as a proton acceptor in acylation reactions. Such amines are tri(lower)alkylamines, e.g., trimethylamine, triethylamine, and the like, pyridine, dimethylaniline, N-methylpiperidine, and the like.

A preferred embodiment of the present invention is the process of preparing compounds having the formula

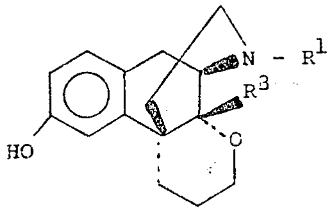

XXXX wherein $R^1$ is selected from the group comprising —$CH_2$—C ≡CH, —$CH_2$—CH═$CH_2$,

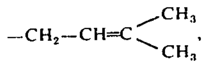

H, (lower)alkyl,

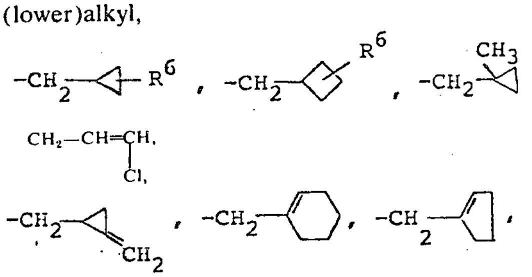

and $C_{3-7}$ alkenyl in which $R^6$ is H or $CH_3$, $R^3$ is H or (lower)alkyl; which process comprises the consecutive steps of A. treating the compound having the formula

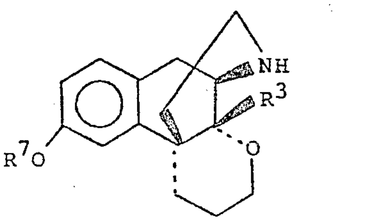

XXXXIIIa in which $R^7$ is (lower)alkyl and $R^3$ is as defined above, with an alkylating or acylating agent having the formula

X—(Z)—W in which W is a radical selected from the group comprising —C ≡CH, —CH═$CH_2$,

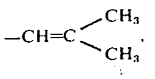

H, (lower)alkyl,

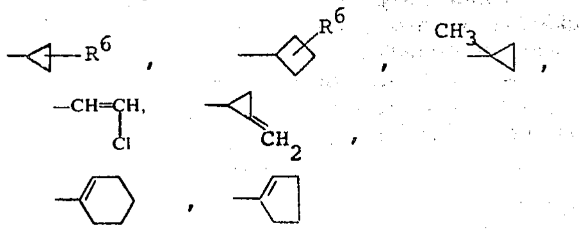

and $C_{2-6}$ alkenyl in which $R^6$ is H or $CH_3$, Z is carbonyl

or $-CH_2-$ and X is chloro, bromo or iodo, in an inert organic solvent in the presence of an appropriate base to produce the compound having the formula

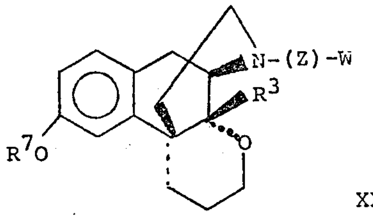

XXXXIVa in which $R^3$, Z, W and $R^7$ are as defined above; and when Z is carbonyl

B. treating compound XXXXIVa with lithium aluminum hydride, in an organic solvent, to produce the compound having the formula

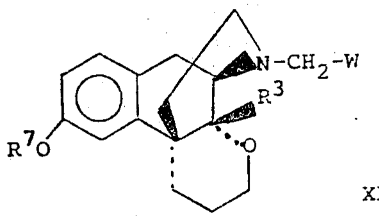

XXXXVa in which $R^7$, W and $R^3$ are as defined above; and

C. cleaving the ether function of compound XXXXIVa or XXXXVa by treatment with an agent selected from the group comprising NaS—$C_2H_5$, hydrobromic acid, boron tribromide or pyridine hydrochloride.

Another preferred embodiment is the process for preparing compounds having the formula

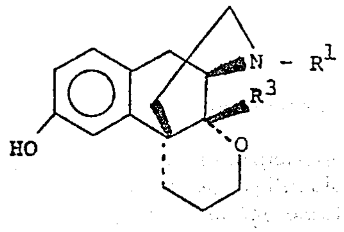

XXXXb wherein $R^1$ is selected from the group comprising $-CH_2-C\equiv CH$, $-CH_2-CH=CH_2$,

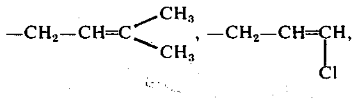

and $C_{3-7}$ alkenyl and $R^3$ is H or (lower) alkyl; which process comprises the consecutive steps of A. treating the compound having the formula

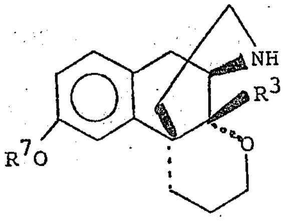

XXXXIIIa in which $R^7$ is (lower)alkyl and $R^3$ is as defined above; with an alkylating agent having the formula $R^1$-X in which $R^1$ is as above and X is chloro, bromo or iodo, in an inert organic solvent in the presence of an appropriate base to produce the compound having the formula

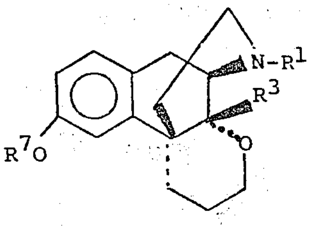

XXXXIVb in which $R^7$, $R^1$ and $R^3$ are as defined above; and

B. cleaving the ether function of compound XXXXIVb by treatment with NaS-$C_2H_5$, boron tribromide or pyridine hydrochloride.

More preferred embodiments are the process for the preparation of compounds of formula XXXXb wherein;

1. In step A $R^7$ is methyl, $R^3$ is H or methyl; the inert organic solvent is methylene chloride, dichloroethane or a (lower)alkanol, the base is pyridine, triethylamine or an alkali metal hydroxide or carbonate and the reaction is conducted at about 15° C. to about reflux temperature.

2. In step A $R^7$ is methyl, $R^3$ is H or methyl; the organic solvent is methanol, ethanol, n-propanol or isopropanol, the base is triethylamine or sodium or potassium carbonate and the reaction is conducted at about reflux temperature for about 5 to about 20 hours.

A preferred embodiment of the present invention is the process for the preparation of the compound having the formula

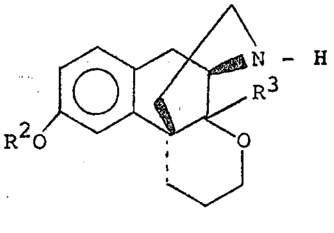

XII in which $R^2$ is (lower)alkyl and $R^3$ is H or (lower)alkyl, which process comprises the consecutive steps of A. hydrating the compound having the formula

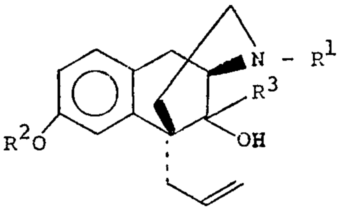

VII in which $R^1$ and $R^2$ are (lower)alkyl and $R^3$ is H or (lower)alkyl, by treatment with borane, alkali metal base (sodium hydroxide) and hydrogen peroxide to produce the compound having the formula

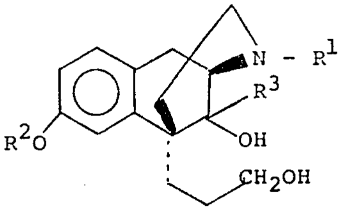

VIII in which $R_1$, $R^2$ and $R^3$ are as above;

B. sulfonating compound VIII with a large excess of a (lower)alkyl or arylsulfonyl halide to produce the compound having the formula

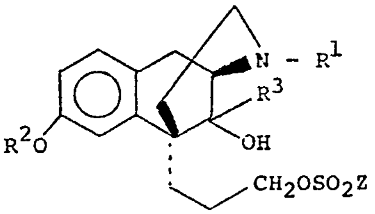

IX in which $R^2$, $R^3$ and $R^1$ are as above and Z is (lower)alkyl or aryl;

C. cyclizing compound IX by treatment with an excess of sodium hydride to produce the compound having the formula

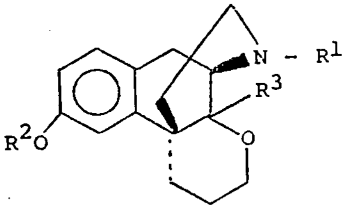

X in which $R^1$, $R^2$ and $R^3$ are as above;

D. treating compound X with cyanogen bromide to produce the compound having the formula

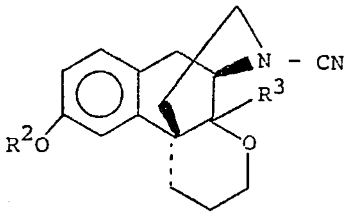

XI in which $R^1$, $R^2$ and $R^3$ are as above; and

E. treating compound XI with lithum aluminum hydride in an inert solvent to produce the compound having the formula XII.

A more preferred embodiment of the present invention is the process for the preparation of the compound having the formula

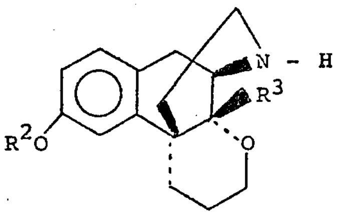

XIIp in which $R^2$ is methyl and $R^3$ is H or (lower)alkyl, which process comprises the consecutive steps of A. hydrating the compound having the formula

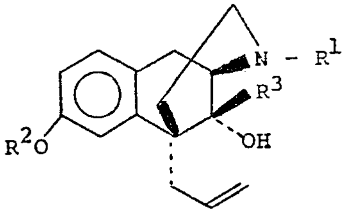

VIIp in which $R^1$ and $R^2$ are methyl and $R^3$ is H or (lower)alkyl, by treatment with an excess of borane, slight excess of an alkali metal hydroxide (sodium hydroxide) and hydrogen peroxide to produce the compound having the formula

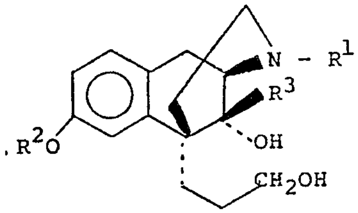

VIIIp in which $R^1$, $R^2$ and $R^3$ are as above;

B. sulfonating compound VIIIp with a large excess of a (lower)alkyl or arylsulfonyl halide to produce the compound having the formula

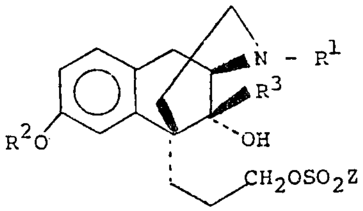

IXp in which $R^2$, $R^3$ and $R^1$ are as above and Z is (lower)alkyl or aryl;

C. cyclizing compound IXp by treatment with an excess of sodium hydride in an inert organic solvent (benzene, toluene, xylene or the like) to produce the compound having the formula

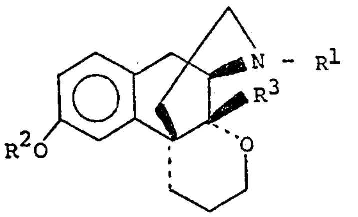

Xp in which $R^1$, $R^2$ and $R^3$ are as above;

D. treating compound X with cyanogen bromide to produce the compound having the formula

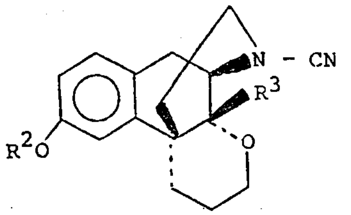

XIp in which $R^1$, $R^2$ and $R^3$ are as above; and

E. treating compound XIp with lithium aluminum hydride in an inert solvent to produce the compound having the formula XIIp.

A more preferred embodiment of the present invention is the process for the preparation of the compound having the formula

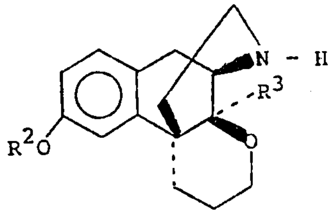

XIIz in which $R^2$ is methyl and $R^3$ is H or (lower)alkyl, which process comprises the consecutive steps of A. hydrating the compound having the formula

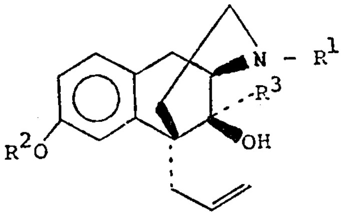

VIIz in which $R^1$ and $R^2$ are methyl and $R^3$ is H or (lower)alkyl, by treatment with an excess of borane, slight excess of an alkali metal hydroxide (sodium hydroxide) and hydrogen peroxide to produce the compound having the formula

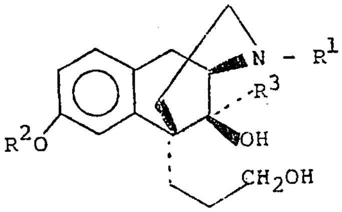

VIIIz in which $R^1$, $R^2$ and $R^3$ are as above; sulfonating compound VIIIz with a large excess of a (lower) alkyl or arylsulfonyl halide to produce the compound having the formula

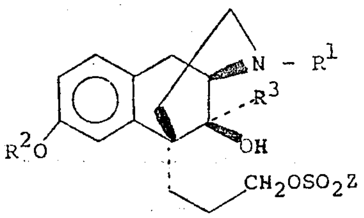

IXz in which $R^2$, $R^3$ and $R^1$ are as above and Z is (lower)alkyl or aryl;

C. cyclizing compound IXz by treatment with an excess of sodium hydride in an inert organic solvent (benzene, toluene, xylene or the like), to produce the compound having the formula

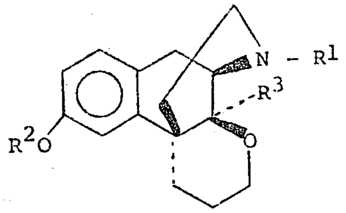

Xz in which $R^1$, $R^2$ and $R^3$ are as above;

D. treating compound Xz with cyanogen bromide to produce the compound having the formula

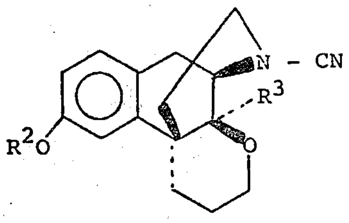

XIz in which $R^1$, $R^2$ and $R^3$ are as above; and

E. treating compound XIz with lithium aluminum hydride in an inert solvent to produce the compound having the formula XIIz.

All of the compounds of the preferred embodiments herein are novel and valuable for their properties as analgesic and/or narcotic antagonist agents, or as intermediates in the preparation of compounds having these biological activities.

In particular, the compounds having the formula XV are those which possess the most desirable properties, i.e., analgesic and/or narcotic antagonist properties. Some of these compounds also possess antitussive activity, a property generally inherent with analgetic activity in similar series.

It is well known in the narcot analgesic prior art that it is possible for some compounds to possess both agonist and antagonist properties. An agonist is a compound that imitates a narcotic analgesic and possesses analgetic qualities. An antagonist is a compound that counteracts the analgetic and euphoric properties of a narcotic analgetic. It is possible for a compound to have both properties. A good example of such a compound is cyclazocine.

In vivo testing was conducted on the compounds designated herein as XVc (racemic mixture), d-XVc (dextrorotatory isomer), l-XVc (levorotatory isomer) and dl-XVd (see examples for structures) to determine their agonist and/or antagonist properties. Table I represents the results of the experiments. The figures reported are the number of milligrams/kilogram of body weight of compound that produced an agonist or antagonist effect in 50% of the mice and rats so tested ($ED_{50}$).

Other combinations would include the narcotic antagonist in combination with anti-anxiety agents such as chlorodiazepoxide and diazepam, or phenothiazines like chlorpromazine, promazine or methotrimeptrazine.

TABLE I

| | ED₅₀ (mg./kg.) Agonist Activity Phenylquinone Writhing Mouse | | Rat | | Oxymorphone[2] Straub Tail | | Antagonist Activity Oxymorphone[3] Narcosis | | Morphine Antagonism[4] Rat Tail Flick | |
|---|---|---|---|---|---|---|---|---|---|---|
| Test Compounds | SC | PO | SC | PO | SC | PO | SC | PO | SC | PO |
| XVc tartrate | 0.19 | N.D. | 0.03 | 4.0 | 0.61 | N.D. | 0.36 | N.D. | 0.05 | 7.3 |
| d-XVc tartrate | >40 | N.D.[5] | χ15 | N.D. | >10 | N.D. | N.D. | N.D. | >20 | N.D. |
| l-XVc tartrate | 0.11 | 2.7 | 0.02 | 1.3 | ≈ 0.2 | 14.6 | 0.014 | 1.25 | 0.021 | 6.3 |
| XVI tartrate | 0.07 | N.D. | ≈0.01 | N.D. | 24 | N.D. | 1.8 | N.D. | 0.9 | N.D. |
| Pentazocine | 4.9 | 36 | N.D. | N.D. | 12.0 | 187 | 10.0 | 90 | 12.2 | 82.2 |
| Nalorphine | 0.77 | 15 | N.D. | N.D. | 1.14 | >64 | 0.58 | 5.4 | 0.38 | 22.1 |
| Levallorphan | 26.3 (poor dose response) | N.D. | N.D. | N.D. | 0.29 | 46 | 0.32 | 5.4 | 0.086 | 12.6 |
| Cyclazocine | 0.047 | 4.0 | N.D. | N.D. | 0.81 | 24 | 0.12 | 2.7 | 0.040 | 3.7 |
| Naloxone | 40 | N.D. | N.D. | N.D. | 0.17 | 13.1 | 0.02 | 0.95 | 0.010 | 2.7 |
| l-XVk hydrochloride | 0.013 | N.D. | 0.009 | N.D. | 0.20 | N.D. | 0.03 | N.D. | 0.97 | N.D. |

All the compounds were tested as the tartrates, but the weights reported in mg./kg. are corrected and reported in terms of the free base.

[1]A 50 per cent reduction in number of phenylquinone induced writhings (Siegmund, E. A. et al., Proc. Soc. Biol. & Med. 95, 729; 1957).

[2]Antagonism of Straub Tail induced by oxymorphone (2 mg./kg. sc.) in 50 per cent of mice.

[3]Antagonism of righting reflex loss induced by oxymorphone (1.5 mg./kg. sc.) in 50 per cent of rats.

[4]A 50 per cent reduction of analgesic effect induced by morphine (15 mg./kg. sc.) as measured by the rat tail flick procedure (Harris, L. S. and Pierson, A. K., J. Pharmacol. & Expt. Therap., 143, 141; 1964).

[5]N.D. - Not done.

It is apparent from the table that compound l-XVc exhibits potent agonist and antagonist activity upon parenteral and oral administration. All the compounds of formula XV of the present invention possess varying degress of potency of the same activity. Similarly, as is inherant in most compounds of this type, the compounds possess some subsidiary anti-tussive activity.

The normal oral and parenteral dosage range of the compounds of formula XV in adult humans is in the range of about 0.1 to 50 mg. 3 to 4 times a day depending upon the route of administration and the particular compound administered.

It has been reported in the literature that the compound haloperidol, 4[4-(p-chlorophenyl)-4-hydroxypiperidino]-4'-fluorobutyrophenone (Merck Index, 8th Edition, p. 515) has found some experimental use in the alleviation of narcotic addiction withdrawal symptoms. It is therefore an embodiment of the present invention to combine haloperiodol with the narcotic antagonists of the instant invention, to produce a product not only preventing narcotic abuse, but at the same time providing supportive therapy in the absence of opiates.

Haloperidol is commonly administered orally in 0.5 to 5.0 mg. two or three times daily depending upon the severity of the illness. A dose of haloperidol in this range would be administered contemporaneously with an effective dose of the narcotic antagonist to produce the desired result.

EXAMPLES

Example 1

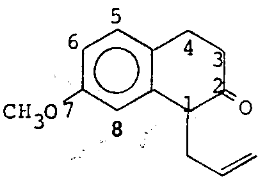

3,4-Dihydro-7-methoxy-1-allyl-2(1H)naphthalenone (IIa).

To a stirred solution of 50 g. (0.284 mole) of Ia (3,4-dihydro-7-methoxy-2(1H)naphthalenone) dissolved in 200 ml. of dry benzene was added during 5-10 minutes and under nitrogen, 40.5 g. (0.5 mole) of pyrrolidine dissolved in 50 ml. of benzene. The mixture was refluxed for one hour and 5 ml. of water was collected in a Dean-Stark apparatus. The mixture was cooled and added slowly to 60.5 g. (0.5 mole) of allyl bromide dissolved in 300 ml. of benzene. The resulting mixture was refluxed for three hours. Then 200 ml. of water was added to the reaction and refluxing was resumed. After 30 minutes the mixture was cooled, the benzene layer was separated, washed with water, followed by water saturated with sodium chloride, dried over sodium sulfate and evaporated to dryness. The residue was distilled to give 52.20 g. (85% yield) of IIa; b.p. 106°–112°/0.01–0.05 mm. The infrared (IR) and Nuclear Magnetic Resonance (NMR) spectra were consistent with the structure.

Anal. calc'd. for $C_{14}H_{16}O_2$: C, 77.74; H, b 7.45. Found: C, 77.47; H, 7.50.

EXAMPLE 2

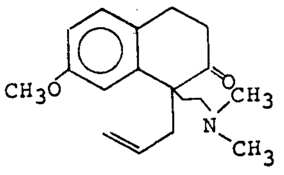

.HBr 3,4-Dihydro-7-methoxy-1-allyl-1-(2-dimethylaminoethyl)-2-(1H)naphthalenone hydrobromide (IIIa).

A mixture of 400 ml. dry benzene, 22 g. (0.25 mole) of tert.-amyl alcohol and 10.62 g (0.25 mole) of sodium hydride was refluxed under $N_2$ for 30 minutes or until all the hydride was consumed. Then 47.2 g. (0.22 mole) of IIa in 100 ml. of benzene was added slowly while distilling off the excess of amyl alcohol. Another 100 ml. of benzene was added and distilled off. Then 28 g. (0.3 mole) of 2-chloro-N,N-dimethylaminoethane in 100 ml. of benzene was added dropwise. The reaction mixture was refluxed for 20 hours, washed twice with water, and diluted with ether and extracted with 1N HCl. The acidic extract was warmed to 60° C. for one hour, cooled and extracted with ether to recover 15 g. of IIa. The acidic extract was then cooled, basified with $NH_4OH$ and extracted with ether. It was dried over potassium carbonate, treated with charcoal and after filtration, with dry HBr. There was obtained 33.87 g. (61.5%) of HBr salt of IIIa. After recrystallization from methanol/ether it melted at 139°–140°. The IR and NMR were consistent with the structure.

Anal. calc'd. for $C_{18}H_{25}NO_2$.HBr: C, 58.69; H, 7.11; N, 3.80. Found: C, 58.63; H, 7.16; N, 3.59

EXAMPLE 3

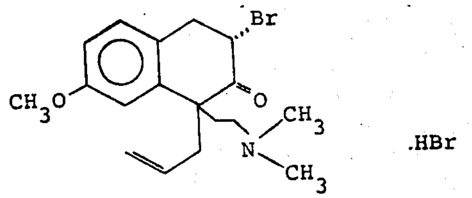

3-Bromo-3,4-dihydro-7-methoxy-1-allyl-1-(2-dimethylaminoethyl-2-(1H)naphthalenone hydrobromide (IVa).

To a stirred solution of 15 g. (41 mmole) of IIIa in 100 ml. of methylene chloride and 300 ml. tetrahydrofuran (THF) in the dark, a solution of 20.58 g. (41.5 mmole) pyrrolidone hydrotribromide in 300 ml. of THF was added over a 4 hour period. After the addition, the reaction mixture was left overnight at room temperature. The solvents were evaporated to dryness and the solid residue recrystallized from 700 ml. of isopropanol to give 12.7 g. (68.5%) of IVa; m.p. 149°–150° C. The IR and NMR were consistent with the structure.

Anal. calc'd for $C_{18}H_{24}NO_2Br$.HBr: C, 48.34; H, 5.63; N, 3.13. Found: C, 48.64; H, 5.70; N, 3.14

EXAMPLE 4

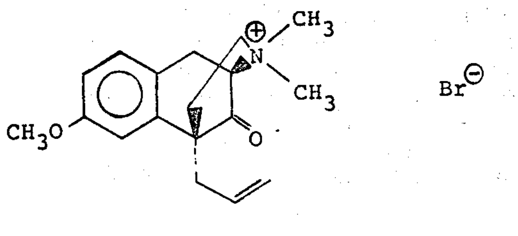

2'-Methoxy-2-methyl-5-allyl-9-oxo-6,7-benzomorphan methobromide (Va).

The HBr salt IVa (12.6 g., 0.028 mole) was dissolved in ice cold water, placed in a separatory funnel and covered with ether. Enough concentrated ammonium hydroxide was added to alkalinize the mixture and the free base of IV was extracted and separated as rapidly as possible. The ether was evaporated, and the residue was dissolved in acetone and left overnight. There was obtained 6.55 g. (65.5% yield) of solid Va. After recrystallization from isopropanol, it melted at 175°–177° C. The IR and NMR were consistent with the structure.

Anal. calc'd for $C_{17}H_{21}NO_2.CH_3Br.\frac{1}{2}H_2O$: C, 57.60; H, 6.71; N, 3.73. Found: C, 57.44; H, 6.78; N, 3.58.

EXAMPLE 5

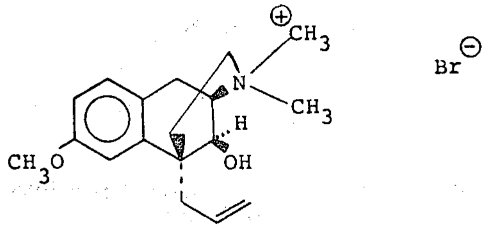

2'-Methoxy-2-methyl-5-allyl-9β-hydroxy-6,7-benzomorphan methobromide (VIa).

To a stirred suspension of Va [5.9 g., 0.0161 mole] in 50 ml. of anhydrous ethanol, was added 0.350 g. (.009 mole) of $NaBH_4$. One hour after the addition, 0.8000 g. of 48% HBr diluted with 10 ml. of water was added in small portions, and the reaction mixture was evaporated to dryness. The residue was taken up into methylene chloride, the inorganic material was filtered off and the solution was dried over sodium sulfate and evaporated to dryness. The solid residue was dissolved in a minimum of isopropanol and enough ether was added to crystallize VIa. There was obtained 4.2 g. of VIa (72.3% yield); m.p. 193° C. The IR and NMR spectra were consistent with the structure.

Anal. calc'd. for $C_{17}H_{23}NO_2.CH_3Br$: C, 58.69; H, 7.11; N, 3.80. Found: C, 58.89; H, 7.26; N, 3.71

EXAMPLE 6

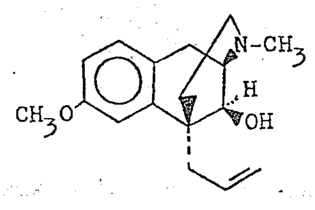

2'-Methoxy-2-methyl-5-allyl-9β-hydroxy-6,7-benzomorphan (VIIa).

To 50 ml. of boiling 1-octanol was added 4.87 g. (13.2 mmole) of VIa and the mixture was refluxed for 15 minutes. After cooling, the solution was diluted with ether and extracted with 2N HCl followed by two portions of 20 ml. of $H_2O$. The aqueous extracts were washed with petroleum ether (essentially n-hexane) to eliminate the traces of octanol, basified with ammonium hydroxide and extracted with ether, dried over sodium carbonate and evaporated. The oily residue crystallized upon addition of cyclohexane. Recrystallization from cyclohexane afforded 2.2 g. of VIIa in a yield of 61% m.p. 93°–94° C. The IR and NMR spectra are consistent with the structure.

Anal. calc'd for $C_{17}H_{23}NO_2$: C, 74.69; H, 8.48; N, 5.12. Found: C, 74.64; H, 8.49; N, 5.12.

EXAMPLE 7

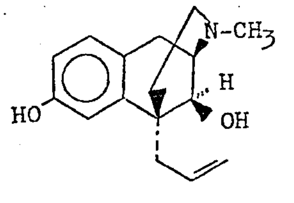

2'-Hydroxy-2-methyl-5-allyl-9β-hydroxy-6,7-benzomorphan (VIIIa).

A solution of 1 g. of VIIa (0.037 mole) in 20 ml. of dry methylene chloride was added slowly to a cooled (−10° C.) solution of 0.927 g. (.037 mole) of $BBr_3$ in 20 ml. of methylene chloride. Upon completion of the addition, the ice bath was removed and the reaction mixture was left at room temperature overnight. The content of the flask was poured on crushed ice and concentrated ammonium hydroxide, followed by extraction with chloroform. After drying over sodium sulfate, there was obtained 0.46 g. of VIIIa as a solid; yield: 48%. It was recrystallized from toluene-petroleum ether; m.p. 60°–64° C. The IR and NMR spectra are consistent with the structure.

Anal. calc'd. for $C_{16}H_{21}NO_2$: C, 74.09; H, 8.16; N, 5.40. Found: C, 74.73; H, 8.25; N, 5.30.

EXAMPLE 8

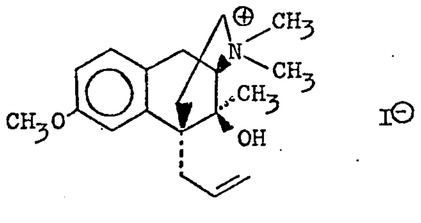

2'-Methoxy-2,9α-dimethyl-5-allyl-9β-hydroxy-6,7-benzomorphan methiodide (VIb).

To 5 g. (13.6 mmole) of Va was added rapidly a solution of Grignard reagent prepared from 11.35 g. (79 mmole) methyliodide and 2.07 g. (85.0 mole) magnesium in 50 ml. of ether. After the addition, the reaction was stirred at room temperature until all the solid had dissolved (approximately two hours), then water (5 ml.) was added to the solution while cooling, followed by 15 ml. of 5N HCl and 5 g. of potassium iodide dissolved in 10 ml. of water. After stirring for two additional hours, the solid was filtered off. The product was recrystallized from water to give 4.3 g. (78% yield) of VIb; m.p. 184°–185° C. The IR and NMR wee consistent with the structure.

Anal. calc'd for $C_{18}H_{25}NO_2.CH_3I.\frac{1}{2}H_2O$: C, 52.06; H, 6.66; N, 3.19. Found: C, 52.31; H, 6.56; N, 3.19.

EXAMPLE 9

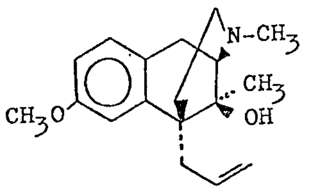

2'-Methoxy-2,9α-dimethyl-5-allyl-9β-hydroxy-6,7-benzomorphan (VIIb).

To 75 ml. of boiling 1-octanol was added 9.00 g. of VIb (0.021 mole) and the mixture refluxed for 15 minutes. After workup, as described in example 6, there was obtained 4.62 g. of VIIb as an oil which crystallized upon standing; m.p. 57° C. (Yield 75.5%). An oxalate salt was prepared and recrystallized from a mixture of methanol and ethyl ether; m.p. 180° C. (change 165°–175°). The IR and NMR spectra were consistent with the structure.

Anal. calc'd. for $C_{18}H_{25}NO_2.C_2H_2O_4.\frac{1}{2}CH_3OH$: C, 62.49; H, 7.54; N, 3.55. Found: C, 62.55; H, 7.19; N, 3.81

EXAMPLE 10

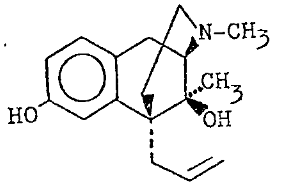

2'-Hydroxy-2,9α-dimethyl-5-allyl-9β-hydroxy-6,7-benzomorphan (VIIIb).

To a stirred and ice-salt cooled solution of 0.450 g. (1.7 mmole) $BBr_3$ in 10 ml. of methylene chloride was added slowly 0.500 g. (1.7 mmole) of VIIa dissolved in 10 ml. of dry methylene chloride. After working up the reaction mixture as in example 7, there was obtained 0.47 g. of crude VIIIb. The crude material was dissolved in acetone and precipitated by oxalic acid. There was obtained 0.300 g. of the oxalate salt of VIIIb (47.5% yield). It was recrystallized from acetone; m.p. 195° (dec.). The IR and NMR spectra were consistent with the structure.

Anal. calc'd for $C_{17}H_{23}NO_2.C_2H_2O_4$: C, 62.79; H, 6.93; N, 3.85. Found: C, 63.00; H, 7.01; N, 4.04

EXAMPLE 11

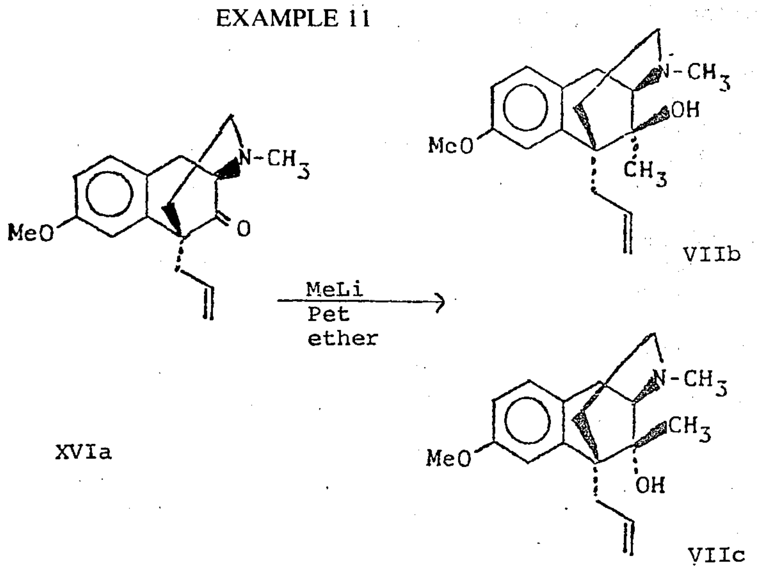

XVIa VIIb VIIc

5-Allyl-2'-methoxy-2,9-dimethyl-9α-hydroxy-6,7-benzomorphan (VIIb & VIIc).

A solution of methyllithium in ether (71 ml of a 5% solution, 115 mmol) was transferred with a syringe to a two liter flask under $N_2$, evaporated to dryness and covered with 500 ml of dry petroleum ether. To the vigorously stirred suspension (under $N_2$) thus obtained, was added dropwise a solution of 14.60 g (53.8 mmol) XVIa in 250 ml of dry petroleum ether (30–65). The reaction mixture was then stirred at 20°–25° for 19 hours. A solution of methyllithium in ether (15 ml of a 5% solution, 24 mmol) was added and the mixture stirred for 1.5 hours to complete the reaction. Water was slowly added to destroy the excess of methyllithium and the organic phase was washed with water.

The water phase was extracted with ether, dried over sodium sulfate, and evaporated to dryness leaving 14.51 g (93%) of oil which was a mixture of VIIb (40%) and VIIc (60%) (estimated by NMR). The NMR spectrum showed two distinct signals for

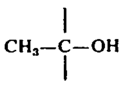

at δ= 1.0 (II) and δ= 1.58 (III) based on TMS (tetramethylsilane). After treatment with charcoal, the free base (13.05 g) was dissolved in 90 ml of 95% ethanol and added to a boiling solution of 11.96 g of picric acid in 150 ml of 95% ethanol.

The solution was kept at 5° for 60 hours and 21.88 g of a yellow solid which was a mixture of VIIb and VIIc (20:80) was filtered. Two recrystallizations from dioxane and 95% ethanol afforded 15.3 g (58%) of the α-isomer VIIc m.p. 209°–12°.

Treatment of the free base with oxalic acid in methanol and ether gave a solid which after recrystallization afforded an analytical sample, m.p. 208°– 209° (VIIc).

Anal. calc'd. for $C_{18}H_{25}NO_2.C_2H_2O_4$ C = 63.78; H = 7.21; N — 3.71. Found: C=63.78; H=7.41; N=3.92

The mother liquor was concentrated and 6.16 g (24%) of the β-isomer VIIb crystallized out. Recrystallization from acetone ether gave a sample melting at 175°–8°. The free base was found to be identical with a sample obtained from example 9. The IR and NMR spectra were consistent with the structures.

EXAMPLE 12

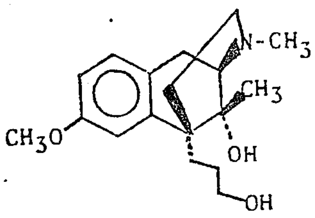

9α-Hydroxy-2'-methoxy-2,9β-dimethyl-5-(propan-3-ol)-6,7-benzomorphan (VIIIc).

To a cooled (−10°, ice bath) solution of 0.69 g (2.4 mmol) VIIc in 24 ml of tetrahydrofuran was added 9.6 ml (9.6 mmol) of a 1M solution of borane in tetrahydrofuran. After 4 hours, 10 ml of a 1N solution of sodium hydroxide was added (dropwise for the first 0.5 ml) and 1.26 g (10.0 mmol) of a 30% solution of hydrogen peroxide. After stirring for 1 hour at 20°–25° the solution was acidified with 20 ml of 1N hydrochloric acid, kept at 20°–25° for 0.5 hour and refluxed for 1 hour. The solvent was then evaporated in vacuo, the residue dissolved in dilute ammonium hydroxide and extracted with methylene chloride (4 × 100 ml). The extracts were washed with water, dried ($Na_2SO_4$) and evaporated to dryness leaving 0.77 g of an oil which was crystallized from benzene yielding 0.61 g (83%). A sample obtained from tetrahydrofuran-petroleum ether melted at 152°–4° (VIIIc).

Anal. calc'd. for $C_{18}H_{27}NO_3$: C, 70.79; H, 8.91; N, 4.59. Found: C, 71.17; H, 9.04; N, 4.44

The IR and NMR spectra were consistent with the structure.

EXAMPLE 13

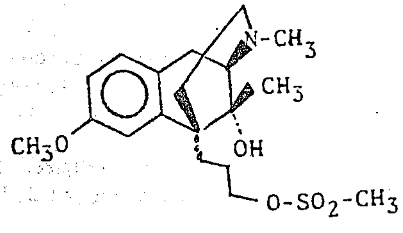

9α-Hydroxy-2′-methoxy-2,9β-dimethyl-5-(propane-3-mesylate)-6,7-benzomorphan (IXc).

To a solution of 0.61 g (2.0 mmol) VIIIc 20 ml of dry tetrahydrofuran and 2 ml of pyridine was added 1.14 g (10 mmol) of mesyl chloride. After stirring for 3 hours at 20°, the solution was concentrated in vacuo, the oily residue dissolved in 250 ml of dilute hydrochloric acid and extracted with methylene chloride. The extract was washed with water, dried ($Na_2SO_4$) and evaporated in vacuo leaving 0.85 g of light yellow oil. The hydrochloric acid salt was crystallized from methanol-ether yielding 0.61 g (79%) of IXc. Recrystallization from methanol-ether afforded an analytical sample, m.p. 143°-5°.

Anal. calc'd. for $C_{25}H_{32}N_4O_{12}S$: C, 49.01; H, 5.27; N, 9.15. Found: C, 49.03; H, 5.26; N, 9.16

Treatment of the free base with picric acid in acetone-ether gave the corresponding picrate, m.p. 156°—7°.

Anal. calc'd. for $C_{19}H_{39}ClNO_5S$: C, 54.34; H, 7.20; N, 3.34. Found: C, 54.17; H, 7.23; N, 3.26

The IR and NMR spectra were consistent with the structure.

EXAMPLE 14

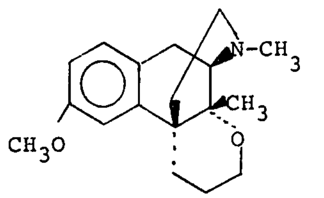

3-Methoxy-14β--methyl-N-methyl-8-Oxamorphinan (Xc).

To a solution of 1.38 g (4.5 mmol) VIIIc in 50 ml of tetrahydrofuran and 5 ml of pyridine was added 1.76 ml (2.59 g, 22.5 mmol) of mesyl chloride. After stirring for 3 hours at 20°, the solvent was evaporated in vacuo, the residual oil dissolved in dilute hydrochloric acid and extracted with ether. The water phase was then basified with ammonium hydroxyde and extracted with methylene chloride. The methylene chloride extracts were washed with water, dried ($Na_2SO_4$) and evaporated in vacuo leaving 1.89 g of brown oil. The crude oil thus obtained was dissolved in 30 ml of dry dimethylformamide placed in a flask under nitrogen, cooled to 0°C (ice-salt bath) and treated with 0.43 g (9.0 mmol) of a 57% dispersion of sodium hydride in mineral oil washed twice with benzene. The cold bath was removed and the reaction mixture was stirred at 20° for 16 hours. The solution was cooled and the excess of sodium hydride was destroyed by careful addition of water. The solvent was evaporated in vacuo leaving a semi-solid residue which was dissolved in water, basified with ammonium hydroxide and extracted with methylene chloride. The organic extracts were washed with water, dried ($Na_2SO_4$) and evaporated in vacuo leaving 1.28 g of brown oil. Dry column chromatography of the residue on an alumina column using chloroform as eluent gave 0.98 g (76%) of pure Xc. The hydrochloric acid salt was recyrstallized from methanol-ether to give a sample melting at 242°-44°.

Anal. calc'd. for $C_{18}H_{26}ClNO_2$: C, 66.76; H, 8.09; N, 4.33. Found: C, 66.35; H, 7.93; N, 4.12

The IR and NMR were consistent with the structure.

EXAMPLE 15

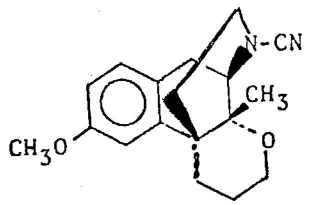

N-Cyano-3-methoxy-14β-methyl-8-oxamorphinan (XIc).

A solution of 0.17 g (1.6 mmol) cyanogen bromide in 5 ml of chloroform was added dropwise to a solution of 0.38 g (1.3 mmol) Xc in 5 ml of chloroform. After refluxing for 22 hours, the solvent was evaporated in vacuo and the residual oil crystallized from methanol giving 0.25 g (64%). The mother liquor was chromatographed on a column of silica gel. Elution with chloroform and 2.5% methanol-chloroform afforded 0.13 g (33%) of XIc. An analytical sample m.p. 157°-8° was recrystallized from methanol.

Anal. calc'd. for $C_{18}H_{22}N_2O_2$: C, 72.45; H, 7.43; N, 9.39. Found: C, 72.45; H, 7.50; N, 9.35.

The IR and NMR were consistent with the structure.

EXAMPLE 16

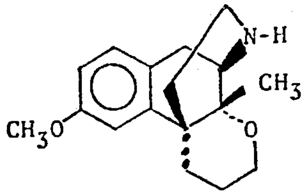

3-Methoxy-14β-methyl-8-oxamorphinan (XIIc).

A solution of 0.60 g (2 mmol) XIc in 15 ml of dry tetrahydrofuran was slowly added to a cooled (0°) and stirred solution of 0.30 g (8 mmol) lithium aluminum hydride in 30 ml of tetrahydrofuran under nitrogen. The reaction mixture was stirred at 0° for 15 min., gradually heated and refluxed for 3 hours. After cooling to 0°, 0.3 ml of water, 0.22 ml of 20% sodium hydroxide and 1.05 ml of water were successively added. The reaction mixture was stirred at 20° for 20 min, the solid was filtered off and the filtrate evaporated to dryness leaving 0.69 g of an oil which was crystallized as an hydrochloric acid salt from acetone-ether to give 0.50 g (80%). Recrystallization from methanol-ether gave an analytical sample m.p. 270° dec.

Anal. calc'd. for $C_{17}H_{24}ClNO_2$: C, 65.90; H, 7.81; N, 4.52. Found: C, 65.46; H, 7.80; N, 4.52.

The IR and NMR were consistent with the structure.

EXAMPLE 17

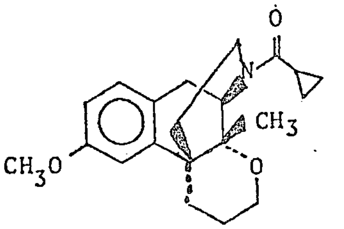

N-Cyclopropylcarbonyl-3-methoxy-14β-methyl-8-oxamorphinan XIIIc.

A solution of 0.532 g (5.08 mmol) cyclopropyl carboxylic acid chloride in 25 ml of methylene chloride was added to a cooled (0°, ice bath) solution of 1.39 g (5.08 mmol) XIIc in 50 ml of methylene chloride and 1.0 ml of triethylamine. After 1 hour at 0°, the reaction mixture was diluted with 300 ml of methylene chloride, washed with 1N hydrochloric acid and water. The organic fraction was dried ($Na_2SO_4$) and evaporated in vacuo leaving 1.97 g of oil which crystallized from ether-pet ether to yield 0.33 g (19%). The mother liquor was chromatographed on an alumina column. Elution with chloroform gave 0.93 g (53%) of amide XIIIc. The analytical sample, m.p. 141°–3° was recrystallized from ether-petroleum ether.

Anal. calc'd. for $C_{21}H_{27}NO_3$: C, 73.87; H, 7.97; N, 4.10. Found: C, 73.56; H, 8.03; N, 3.91.
The IR and NMR were consistent with the structure.

EXAMPLE 18

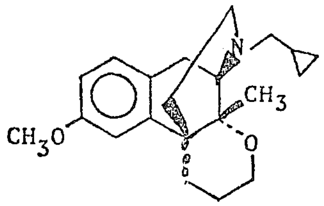

N-Cyclopropylmethyl-3-methoxy-14β-methyl-8-oxymorphinan (XIVc).

To a cooled (ice-salt bath) and stirred solution of 152 mg (4.0 mmol) lithium aluminum hydride in 40 ml of dry tetrahydrofuran was slowly added a solution of 0.69 g (2.0 mmol) XIIIc in 20 ml of dry tetrahydrofuran. The reaction mixture was then refluxed for 2 hours, cooled in an ice-bath and the excess of hydride was destroyed with 0.15 ml of water, 0.11 ml of 20% sodium hydroxide and 0.53 ml of water. The solid was filtered off and the solvent was evaporated in vacuo leaving 0.76 g of colorless oil which was crystallized as hydrochloric acid salt from methanol-ether to give 0.71 g (97%) XIVa. Recrystallization afforded a sample melting at 246°–7°.

Anal. calc'd. for $C_{21}H_{30}ClNO_2$: C, 69.31; H, 8.31; N, 3.85, Found: C, 69.24; H, 8.55; N, 3.75
The IR and NMR were consistent with the structure.

EXAMPLE 19

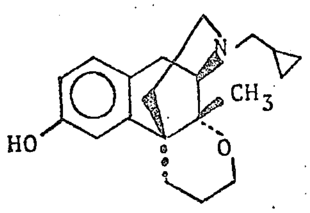

N-Cyclopropylmethyl-3-hydroxy-14β-methyl-8-oxamorphinan XVc. Sodium thioethoxide method.

To a cooled ice bath suspension of 550 mg (13 mmol) of a 57% dispersion of sodium hydride in mineral oil previously washed twice with benzene, in 15 ml of dry dimethylformamide, under nitrogen, was added 1.05 ml, 887 mg (14 mmol) of ethanethiol. The suspension gradually became a clear solution. To the solution thus obtained was added 424 mg (1.3 mmol) of XIVc in 5 ml of dry dimethylformamide and the reaction mixture was gently refluxed for 3 hours. After cooling, the solution was poured on 250 ml of ice and water, the pH was adjusted to ≈8 with dilute hydrochloric acid and the aqueous phase was extracted with methylene chloride (4 × 100 ml). The extracts were dried ($Na_2SO_4$), and evaporated in vacuo (0.4 mm Hg/40°C) for 30 mins. leaving 458 mg of oil which was dry chromatographed on an alumina column. Elution with chloroform afforded 323 mg (79%) of phenol XVc. Crystallization of the hydrochloric acid salt of XVa from methanol-ether-dry HCl gas gave a sample melting at 268°–70°.

Anal. calc'd. for $C_{20}H_{28}ClNO_2$: C, 68.65; H, 8.07; N, 4.00. Found: C, 68.81; H, 8.24; N, 3.79.
The IR and NMR spectra were consistent with the structure.

EXAMPLE 20

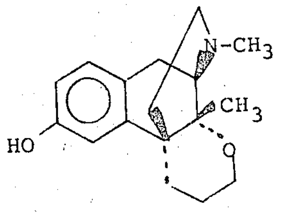

3-Hydroxy-14β-methyl-N-methyl-8-oxymorphinan (XVIIc.

To a cooled (0°) solution of 0.50 g (1.67 mmol) Xc in 30 ml of methylene chloride was added 6.68 mmol) of a 1M solution of boron tribromide in methylene chloride and the solution was stirred at 0° for 2 hours. Then, 1 ml of 1N hydrochloric acid and 10 ml of water were added and the solution was stirred without cooling for 20 min. The reaction mixture was diluted with 200 ml of water and extracted with methylene chloride. The organic fraction was washed with water, dried ($Na_2SO_4$) and evaporated in vacuo leaving 0.48 g of amorphous material which was dry chromatographed on an alumina column. Elution with 5% methanol in chloroform gave 0.28 (59%) of the phenol XVIIc. The hydrochloric acid salt of XVIIc was recrystallized from methanol-ether m.p. 258°–60°.

Anal. calc'd. for $C_{17}H_{24}ClNO_2 + ½ CH_3OH$: C, 64.50; H, 8.04; N, 4.30. Found: C, 64.64; H, 7.97; N, 4.34.
The IR and NMR spectra were consistent with the structure.

EXAMPLE 21

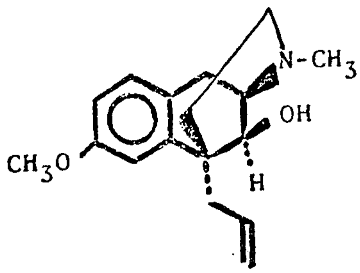

5-Allyl-9β-hydroxy-2′-methoxy-2-methyl-6,7-benzomorphan VIId.

A solution of 0.27 g (1 mmol) XVIa in 10 ml of ethanol was added to a solution of 45 mg of sodium borohydride in 10 ml of ethanol and the reaction mixture was refluxed for 1 hours. After cooling, the reaction mixture was neutralized with dilute HCl and the solvent was evaporated. The residue was treated with dilute ammonium hydroxide and extracted with methylene chloride. The organic phase was dried over sodium sulfate and evaporated to dryness yielding 0.24 g (88%) of oil which crystallized from ether-petroleum ether; mp. 89.5°–90.5°.

The IR and NMR spectra were consistent with the structure.

EXAMPLE 22

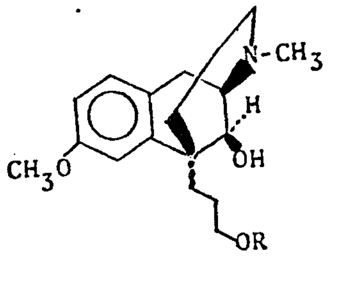

9β-Hydroxy-2′-methoxy-2-methyl-5(propan-3-ol)-6,7-benzomorphan (VIIId).

To a cooled ice-salt bath solution of 2.18 g (8.0 mmol) XII in 80 ml of tetrahydrofuran there was added 28.0 ml (28.0 mmol) of 1M solution of tetrahydrofuran borane complex. After stirring for 5 hours at −10°, 28.0 ml (28.0 mmol) of a 1N sodium hydroxide solution was slowly added and then 0.91 g (8.0 mmol) of a 30% solution of hydrogen peroxide. After stirring at 20° for 1 hour the solvent was evaporated in vacuo and the residual aqueous phase extracted with ether. The organic extracts were dried ($K_2CO_3$) and evaporated in vacuo leaving 2.72 g of residue which was dissolved in 25 ml of dioxane and 25 ml of glacial acetic acid. After refluxing for 30 mins. the solvent was evaporated under reduce pressure giving an oil which was diluted with water basified and extracted with ether. The combined extracts were dried ($K_2CO_3$) and evaporated to dryness to yield 2.64 g of a yellow oil which was chromatographed on an alumina column. Elution with 1:1 petroleum ether-chloroform gave 0.30 g (14%) of the acetate of VIIId which was distilled at 160–5/ 0.01 mmHg.

Anal. calcd for $C_{19}H_{27}NO_4$: C, 68.44; H, 8.16; H, 4.20. Found: C, 68.28; H, 8.32; N, 3.92.

Elution with 1:19 and 1:9 methanol-chloroform gave 1.71 g (74%) of diol VIIId which was crystallized from ether affording an analytical sample m.p. 98° – 100°.

Anal. calcd. for $C_{17}H_{25}NO_3$: C, 70.07; H, 8.65; N, 4.81. Found: C, 70.16; H, 8.79; N, 4.79.

The IR and NMR spectra were consistent with the structures.

EXAMPLE 23

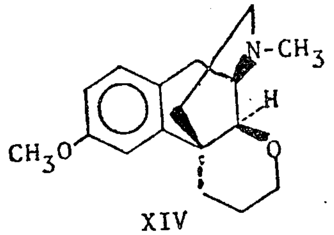

XIV

3-Methoxy-N-methyl-8-oxaisomorphinan (Xd).

To a cooled ice bath solution of 1.08 g (3.71 mmol) VIIId in 15 ml of methylene chloride and 0.12 ml of pyridine there was added 0.369 ml, [0.544 mg (5.19 mmol)] of mesyl chloride. After stirring for 24 hours at 20°, the solution was diluted with water, acidified with 1N hydrochloric acid and extracted with 100 ml of methylene chloride. The aqueous phase was basified with ammonium hydroxide and extracted with methylene chloride (3 × 100 ml). The combined basic extracts were dried ($K_2CO_3$) and evaporated in vacuo leaving 1.48 g of an oil IXd.

The oil thus obtained was dissolved in 35 ml of dry dimethylformamide and placed in a flask under nitrogen. A suspension in 10 ml of dimethylformamide of 0.62 g of a 57% dispersion of sodium hydride in mineral oil washed twice with petroleum ether, was added. After stirring at 20° for 13 hours, the excess of hydride was destroyed with water and the solvent was evaporated in vacuo leaving 1.22 g of brown oil. The residue was chromatographed on an alumina column. Elution with chloroform gave 0.85 (84%) of Xd which was crystallized from ether-petroleum ether affording a sample melting at 104°–5°.

Anal. calcd. for $C_{17}H_{23}NO_2$: C, 74.69; H, 8.48; N, 5.12. Found: C, 74.74; H, 8.58; N, 5.11.

Elution with 1:19 methanol-chloroform gave 0.21 g (16%) of starting material.

The IR and NMR spectra were consistent with the structure.

EXAMPLE 24

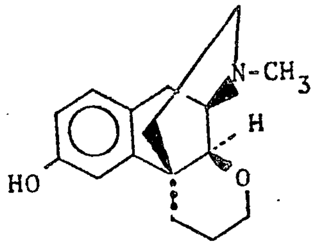

3-Hydroxy-N-methyl-8-oxaisomorphinan XVIId.

To a cooled ice bath solution of 285 mg (1.05 mmol) Xd in dry methylene chloride was added 4.16 mml (4.16 mmol) of a 1N solution of boron tribromide in methylene chloride. After stirring for 1 hour at 0° the mixture was diluted with water, basified with ammonium hydroxide and extracted with methylene chloride. The combined extracts were dried ($K_2CO_3$) and evaporated in vacuo leaving 339 mg of solid material which was crystallized from acetone-methylene chloride giving 315 mg (94%) of XVIId. A sample m.p. 215°–19° was obtained from acetone.

Anal. calcd. for $C_{16}H_{21}NO_2$: C, 74.10; H, 8.16; N, 5.40. Found: C, 74.21; H, 8.37; N, 5.25.
The IR and NMR spectra were consistent with the structure.

EXAMPLE 25

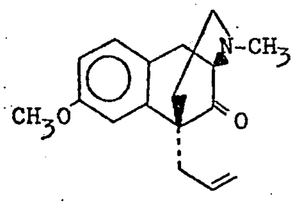

2'-Methoxy-2-methyl-5-allyl-9-oxo-6,7-benzomorphan XVIa.

A suspension of 2 g. (5.46 mmole) Va in 25 ml. 1-octanol was heated under reflux and nitrogen atmosphere for 15 minutes. After cooling the mixture was poured into 40 ml. of 0.5N HCl and extracted twice with 100 ml. of petroleum ether to remove octanol. The water layer was basified with aqueous ammonia and the free base extracted with benzene to yield, after drying and evaporation of solvent, 1.23 g. of an oil XVIa. The oil was stirred with a solution of 350 mg. oxalic acid in 5 ml. water for one hour, and it was left at 5° for 16 hours. Separated solid was filtered off to yield 980 mg. (47%) of XVIa oxalate, containing one mole of water of crystallization; m.p. 156°–162° C. The product recrystallized from water melted at 160°–161° C. with loss of water at 110° C.

Anal. calc'd. for $C_{17}H_{21}NO_2.C_2H_2O_4.H_2O$; C, 60.15; H, 6.64; N, 3.69. Found: C, 60.52; H, 6.72; N, 3.70. The IR and NMR spectra were consistent with the structure.

EXAMPLE 26

N-Cyano-3-methoxy-8-oxaisomorphinan (XId).

Substitution in the procedure of Example 15 for compound Xc used therein of an equimolar quantity of Xd produces the compound XId.

EXAMPLE 27

3-Methoxy-8-oxaisomorphinan (XIId).

Substitution in the procedure of Example 16 for compound XIc used therein of an equimolar quantity of XId produces the compound XIId.

EXAMPLE 28

N-Cyclopropylcarbonyl-3-methoxy-8-oxaisomorphinan (XIIId).

Substitution in the procedure of Example 17 for compound XIIc used therein of an equimolar quantity of XIId produces the compound XIIId.

EXAMPLE 29

N-Cyclopropylmethyl-3-methoxy-8-oxaisomorphinan (XIVd).

Substitution in the procedure of Example 18 for compound XIIIc used therein of a equimolar quantity of XIIId produces compound XIVd.

EXAMPLE 30

N-Cyclopropylmethyl-3-hydroxy-8-oxaisomorphinan (XVd).

Substitution in the procedure of Example 19 for compound XIVc used therein of an equimolar quantity of XIVd produces compound XVd.

EXAMPLE 31

N-Cyclobutylcarbonyl-3-methoxy-14β-methyl-8-oxamorphinan (XIIIe).

A solution of 1.37 g (11 mmol) cyclobutylcarboxylic acid chloride in 20 ml of methylene chloride was added to a cold (0°, ice bath) solution of 2.86 g (10 mmol) XIIc in 30 ml of dry methylene chloride and 1.66 ml (1.21 g; 12 mmol) of triethylamine. The reaction mixture was left for 20 min at room temperature, diluted with 250 ml of methylene chloride, washed with N hydrochloric acid, water, N sodium hydroxide and water. The organic phase was dried ($Na_2SO_4$) and evaporated in vacuo leaving 3.43 g (93%) of XIIIe. The analytical sample was crystallized from ether; m.p. 166° – 7°. The IR and NMR spectra were consistent with the structure.

Anal. calc'd. for $C_{22}H_{29}NO_3$: C, 74.33; H, 8.22; N, 3.94. Found: C, 74.27; H, 8.25; N, 3.92.

EXAMPLE 32

N-Cyclobutylmethyl-3-methoxy-14β-methyl-8-oxamorphinan (XIVe).

A solution of 3.43 g (9.7 mmol) XIIIe in 50 ml of dry tetrahydrofuran was added dropwise (10 min) to a stirred solution of 0.74 g (19 mmol) lithium aluminum hydride in 50 ml of tetrahydrofuran. The reaction mixture was gradually heated and refluxed for 30 min. Then cooled (0°, ice bath) and the excess of hydride was destroyed with 0.74 ml of water, 0.55 ml of 20% sodium hydroxide and 2.6 ml of water. The solid was filtered off and the solvent evaporated in vacuo leaving 3.13 g of oil which crystallized from abs. ethanol to afford 0.93 g (28%) of XIVe. The mother liquor was chromatographed over aluminum oxide (dry column). Elution with benzene gave 1.03 g (31%) of XIVe. An analytical sample, m.p. 105° – 7° was recrystallized from abs. ethanol. The IR and NMR spectra were consistent with the structure.

Anal. calc'd. for $C_{22}H_{31}NO_2$: C, 77.38; H, 9.15; N, 4.10. Found: C, 77.84; H, 9.23; N, 4.09.

EXAMPLE 33

N-Cyclobutylmethyl-3-hydroxy-14β-methyl-8-oxamorphinan (XVe).

To a suspension of 1.33 g (32 mmol) of a 57% dispersion of sodium hydride in mineral oil washed (twice with benzene), in 25 ml of dimethyl formamide cooled in an ice bath, under nitrogen, was added dropwise 2.35 ml (32 mmol) of ethanethiol. The cold bath was removed and the reaction mixture was stirred at 20° – 25° until a clear solution was obtained (15 min.). To the solution thus obtained was added a solution of 0.93 g (2.7 mmol) XIVe in 10 ml of dimethylformamide and the reaction mixture was gently refluxed (153°–6°) for 2 hrs.

The cooled mixture was poured into dilute hydrochloric acid, basified with conc. ammonia and extracted with methylene chloride. The organic layer was extracted with N hydrochloric acid and the aqueous extracts basified with conc. ammonia, and extracted with methylene chloride. The organic phase was dried ($Na_2SO_4$), treated with charcoal and evaporated in vacuo affording 1.05 g of oil. The oil was chromatographed over 75 g of silica gel (dry column). Elution with 100 ml of chloroform followed by ether gave 0.70 g (78%) of XVe. The oxalate salt was prepared from methanol-ether. The IR and NMR spectra were consistent with the structure. Recrystallization of the oxalate from ethanol gave a sample melting at 130° – 132°.

Anal. calc'd. for $C_{21}H_{29}NO_2.C_2H_5OH.½C_2H_2O_4$: C, 68.87; H, 8.67; N, 3.35. Found: C, 68.76; H, 8.81; N, 3.31.

EXAMPLE 34

N-Propargyl-3-methoxy-14β-methyl-8-oxamorphinan (XIVf).

A mixture of 1.8 mmole [0.300 g.] of sodium bicarbonate and 0.225 g. (1.8 mmole) of propargyl bromide in 5 ml. of dry dimethylformamide (DMF) is stirred overnight at room temperature. The reaction mixture is then diluted with ether and filtered. The filtrate is extracted with 0.05N HCl, the layers separated and the acidic layer made alkaline with concentrated ammonium hydroxide before extraction with ether. After drying over potassium carbonate, compound XIVf is obtained upon evaporation of the ether in vacuo.

EXAMPLE 35

N-Propargyl-3-hydroxy-14β-methyl-8-oxamorphinan (XVf).

A solution of 1.35 mmole of XIVf in 10 ml. of methylene chloride is added slowly to a solution of 1.4 mmole (0.350 g.) of $BBr_3$ in 10 ml. of methylene chloride maintained at −10° C. The resulting mixture is stirred overnight at room temperature. The contents of the flask are poured on crushed ice and concentrated ammonium hydroxide, followed by extraction with chloroform. After drying over sodium sulfate, the filtrate is evaporated in vacuo to yield compound XVf.

EXAMPLE 36

N-allyl-3-methoxy-14β-methyl-8-oxamorphinan (XIVg).

Substitution in the procedure of Example 34 for the propargyl bromide used therein of an equimolar quantity of allyl bromide produces compound XIVg.

EXAMPLE 37

N-allyl-3-hydroxy-14β-methyl-8-oxamorphinan (XVg).

Substitution in the procedure of Example 35 for the compound XIVf used therein of an equimolar quantity of XIVg produces compound XVg.

EXAMPLE 38

9β-Hydroxy-2'-Methoxy-2,9α-dimethyl-5-(propan-3-ol)6,7-benzomorphan (VIIIJ).

Substitution in the procedure of Example 12 for the compound VIIc used therein of an equimolar quantity of VIIb produces compound VIIIj.

EXAMPLE 39

9β-Hydroxy-2'-methoxy-2,9α-dimethyl-5-(propane-3-mesylate)-6,7-benzomorphan (IXj).

Substitution in the procedure of Example 13 for the compound VIIIc used therein of an equimolar quantity of VIIIj produces compound IXj.

EXAMPLE 40

3-Methoxy-14α-methyl-N-methyl-8-oxaisomorphinan (Xj).

Substitution in the procedure of Example 14 for the compound VIIIc used therein of an equimolar quantity of VIIIj produces compound Xj.

EXAMPLE 41

N-Cyano-3-methoxy-14α-methyl-8-oxaisomorphinan (XIj).

Substitution in the procedure of Example 15 for the compound Xc used therein of an equimolar quantity of Xj produces compound XIj.

EXAMPLE 42

3-Methoxy-14α-methyl-8-oxaisomorphinan (XIIj).

Substitution in the procedure of Example 16 for the compound XIc used therein of an equimolar quantity of XIj produces compound XIIj.

EXAMPLE 43

N-Cyclopropylcarbonyl-3-methoxy-14α-methyl-8-oxaisomorphinan (XIIIj).

Substitution in the procedure of Example 17 for the compound XIIc used therein of an equimolar quantity of XIIj produces compound XIIIj.

EXAMPLE 44

N-Cyclopropylmethyl-3-methoxy-14α-methyl-8-oxaisomorphinan (XIVj).

Substitution in the procedure of Example 18 for the compound XIIIa used therein of an equimolar quantity of XIIIj produces compound XIVj.

EXAMPLE 45

5-Allyl-9α-hydroxy-2'-methoxy-2-methyl-6,7-benzomorphan (VIIk).

A solution of diisobutylaluminum hydride (62 ml. of a 25% solution, ≈60 mmole) was diluted with 150 ml. of dry tetrahydrofuran and cooled at −40° to −50° under $N_2$. Then a solution of 8.58 g. of compound XVIa (31.6 mmole) in 100 ml. of dry tetrahydrofuran was slowly added from a dropping funnel. After one hour, 5 ml. of water was carefully added, and the gelatinous material evaporated. The residue was dissolved in ether, washed with water, dried over sodium sulfate and evaporated to dryness leaving 8.88 g. of oil. Crystallization from ether-petroleum ether (essentially n-hexane) and chromatography of the mother liquor on silica gel afforded 8.23 g. (95%) of title compound. Recrystallization from acetone-ether-petroleum ether gave an analytical sample; m.p. 73°–78° (VIIk).

Anal. calc'd. for $C_{17}H_{23}NO_2$: C, 74.69; H, 8.48; N, 5.12. Found: C, 74.26; H, 8.73; N, 5.19.

EXAMPLE 46

9α-Hydroxy-2'-methoxy-2-methyl-5-(propan-3-ol)6,7-benzomorphan (VIIIk).

Substitution in the procedure of Example 12 for the compound VIIc used therein of an equimolar quantity of VIIk produced compound VIIIk.

EXAMPLE 47

9α-Hydroxy-2'-methoxy-2-methyl-5-(propane-3-mesylate)-6,7-benzomorphan (IXk).

Substitution in the procedure of Example 13 for the compound VIIIc used therein of an equimolar quantity of VIIIk produced compound IXk.

EXAMPLE 48

3-Methoxy-N-methyl-8-oxamorphinan (Xk).

Substitution in the procedure of Example 14 for the compound VIIIc used therein of an equimolar quantity of VIIIk produced compound Xk.

EXAMPLE 49

N-Cyano-3-methoxy-8-oxamorphinan (XIk).

Substitution in the procedure of Example 15 for the compound Xk used therein of an equimolar quantity of Xk produced compound XIk.

EXAMPLE 50

3-Methoxy-8-oxamorphinan (XIIk).

Substitution in the procedure of Example 16 for the compound XIc used therein of an equimolar quantity of XIk produced compound XIIk.

EXAMPLE 51

N-Cyclopropylcarbonyl-3-methoxy-8-oxamorphinan (XIIIk).

Substitution in the procedure of Example 17 for the compound XIIc used therein of an equimolar quantity of XIIk produced compound XIIIk.

EXAMPLE 52

N-Cyclopropylmethyl-3-methoxy-8-oxamorphinan (XIVk).

Substitution in the procedure of Example 18 for the compound XIIIc used therein of an equimolar quantity of XIIIk produced compound XIVk.

EXAMPLE 53 dl-N-Cyclopropylmethyl-3-hydroxy-8-oxamorphinan hydrochloride (XVk).

Substitution in the procedure of Example 19 for the compound XIVc used therein of an equimolar quantity of XIVk produced compound XVk; m.p. 243°–244° C. (see example 68 for the resolution into d and l XVk). The overall yield from compound XVIa was 35%.

EXAMPLE 54

5-Allyl-2'-methoxy-2-methyl-9β-ethyl-9α-hydroxy-6,7-benzomorphan (VIIm).

Substitution in the procedure of Example 11 for the methyllithium used therein of an equimolar quantity of ethyllithium produces compound VIIm (and VIIn, 5-allyl-2'-methoxy-2-methyl-9α-ethyl9β-hydroxy-6,7-benzomorphan).

EXAMPLE 55

9α-Hydroxy-2'-methoxy-2-methyl-9β-ethyl-5-(propan-3-ol)-6.7-benzomorphan (VIIIm).

Substitution in the procedure of Example 12 for the compound VIIc used therein of an equimolar quantity of VIIm produces compound VIIIm.

EXAMPLE 56

3-Methoxy-14β-ethyl-N-methyl-8-oxamorphinan (Xm).

Substitution in the procedure of Example 14 for the compound VIIIc used therein of an equimolar quantity of VIIIm produces compound Xm.

EXAMPLE 57

N-Cyano-3-methoxy-14β-ethyl-8-oxamorphinan (XIm).

Substitution in the procedure of Example 15 for the compound Xc used therein of an equimolar quantity of Xm produces compound XIm.

EXAMPLE 58

3-methoxy-14β-ethyl-8-oxamorphinan (XIIm).

Substitution in the procedure of Example 16 for the compound XIc used therein of an equimolar quantity of XIm produces compound XIIm.

EXAMPLE 59

N-Cyclopropylcarbonyl-3-methoxy-14β-ethyl-8-oxamorphinan (XIIIm).

Substitution in the procedure of Example 17 for the compound XIIc used therein of an equimolar quantity of XIIm produces compound XIIIm.

EXAMPLE 60

N-Cyclopropylmethyl-3-methoxy-14β-ethyl-8-oxamorphinan (XIVm).

Substitution in the procedure of Example 18 for the compound XIIIc used therein of an equimolar quantity of XIIIm produces compound XIVm.

EXAMPLE 61

N-Cyclopropylmethyl-3-hydroxy-14β-ethyl-8-oxamorphinan (XVm).

Substitution in the procedure of Example 19 for the compound XIVc used therein of an equimolar quantity of XIVm produces compound XVm.

EXAMPLE 62

N-Cyclopropylmetnyl-3-hydroxy-14β-methyl-8-oxamorphinan acetate (XXc).

To 1 ml of acetic anhydride is added 0.001 mole of compound XVc and 0.08 g. of pyridine. The resulting solution is refluxed for 1 hour and the solvents evaporated in vacuo. The residue is taken up in ether and washed with dilute ammonium hydroxide and then water. The ether solution is dried over anhydrous sodium sulfate, filtered and evaporated to dryness in vacuo to yield the desired acetate ester, XXc.

EXAMPLE 63

N-Cyclopropylmethyl-3-hydroxy-14β-methyl-8-oxamorphinan 4'-nicotinoate (XXd).

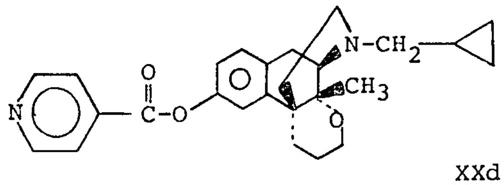

XXd

To a solution of 0.002 mole of compound XVc in 3 ml of pyridine is added 0.0025 mole of 4-nicotinoyl chloride hydrochloride. The mixture is refluxed for one hour and the solvents evaporated. The residue is partitioned between ether and dilute ammonium hydroxide, the ether layer separated, washed with water, dried over anhydrous sodium sulfate, filtered and evaporated in vacuo to produce the desired nicotinoyl ester, XXd.

EXAMPLE 64

N-Cyclopropylmentyl-3-hydroxy-14β-methyl-8-oxamorphinan 3'-nicotinoate-N-oxide (XXe).

Substitution in the procedure of Example 63 for the 4-nicotinoyl chloride hydrochloride used therein of an equimolar quantity of 3-nicotinoyl chloride-N-oxide produces the desired ester, XXe.

EXAMPLE 65

Resolution of (±)-N-Cyclopropylmethyl-3-hydroxy-14β-methyl-8-oxamorphinan into its levo- and dextrorotatory isomers (l-XVc and d-XVc).

A. A solution of 3.37 g (10.8 mmol) racemic XVc free base in 30 ml of acetone was added to a boiling solution of 4.06 g (10.9 mmol) dibenzoyl-d-tartaric acid in 40 ml of methanol and the resulting solution was left at 20° - 25°C, three days to crystallize. The solid thus obtained was recrystallized three times from i-propanol yielding 1.50 g of salt [A]. The mother liquor was evaporated to dryness and the residue was treated with aqueous ammonia to give 2.19 g of material [B].

Dibenzoyl tartarate [A] $[\alpha]_D = -79°$ (C, 0.274; i-Propanol), m.p. 159° - 61°.

The base was liberated with aqueous ammonia to give 0.97 g of *l* isomer (*l*-XVc); $[\alpha]_D = -74°$(C, 0.294; Methanol). The free base was dissolved in methanol and treated with HCl in ether to give on standing at 0°C the hydrochloride. 0.98 g m.p. 281° - 3°. $[\alpha]_D = -73°$ (C, 0.300; Methanol).

Anal. calcd. for $C_{20}H_{27}NO_2$.HCl:C, 68.68; H, 8.06; N, 4.00. Found: C, 68.82; H, 8.21; N, 3.85.

B. The free base [B] 2.19 g (7.0 mmol) was dissolved in 25 ml of acetone and added to a boiling solution of 2.64 g (7.0 mmol) dibenzoyl-1-tartaric acid. The dibenzoyl tartarate which crystallized on standing at 20° - 25°, was recrystallized three times from i-propanol giving 2.32 g of solid, m.p. 153°-4°, of the d isomer (d-XVc).

$[\alpha] = +74°$ (C, 0. 200 g;i-Propanol).

The free base was liberated with aqueous ammonia to give 0.97 g of material.

$[\alpha]_D = +72°$ (C, 0.238; Methanol).

The free base was dissolved in methanol and treated with a solution of HCl in ether giving 0.93 g of hydrochloride, m.p. 283° - 5°.

$[\alpha]_D = +74°$ (C, 0.224; Methanol).

All temperatures expressed in degrees centigrade.

EXAMPLE 66

N-Cyclopropylmethyl-3-hydroxy-14α-methyl-8-oxaisomorphinan (XVj).

Substitution in the procedure of example 19 for the compound XIVc used therein of an equimolar quantity of XIVj produces compound XVj.

EXAMPLE 67

Methoxymethyl ether of N-cyclopropylmethyl-3-hydroxy-14β-methyl-8-oxamorphinan (XXIc).

Chloromethylmethyl ether (0.01 mole) is placed into 10 ml of dry dimethylformamide and the resulting solution is added to 0.0075 mole of N-cyclopropylmethyl-3-hydroxy-14β-methyl-8-oxamorphinan dissolved in 20 ml of dry dimethylformamide. Anhydrous sodium carbonate (0.011 mole) as a fine powder is added to the solution with stirring at about room temperature. Stirring is continued for about five hours. The solution is filtered from the sodium carbonate, evaporated to dryness in vacuo to produce an oil, which is essentially pure XXIc.

Note: The reagent of choice in the O-dimethylation reaction in the 14β- and 14α-methyl compounds is sodium thioethoxide. The use of $BBr_3$ gave moderate success only in the 14α-methyl series.

EXAMPLE 68

Resolution of (±)-N-Cyclopropylmethyl-3-methoxy-8-oxamorphinan into its levo- and dextrorotatory isomers (l-XIVk and d-XIVk).

A. A solution of 10 mmoles of racemic XIVk free base in 30 ml of methanol was added to a boiling solution of 10 mmole of d-dibenzoyltartaric acid in 40 ml of methanol and the resulting solution was allowed to stand several days at 20°-25° C. to crystallize. The solid was collected by filtration and was identified as the tartarate salt of d-XIVk.

B. The mother liquor from step A was evaporated to dryness and the residue was treated with aqueous ammonia to liberate the l-XIVk as the free base. The mixture was extracted with ether. The ether was evaporated to yield crude l-XIVk as an oil. The oil was dissolved in 30 ml of methanol and treated with l-dibenzoyltartaric acid to yield the l-XIVk tartrate salt; m.p. 154°-156° C. The l-XIVk tartrate salt was treated with aqueous ammonia to liberate the free base, which again was collected by extraction with ether, followed by evaporation. The oil so produced was demethylated in example 69 to produce l-XVk as a hydrochloride salt.

EXAMPLE 69 l-N-cyclopropylmethyl-3-hydroxy-8-oxamorphinan hydrochloride (l-XVk).

Substitution in the procedure of example 19 for the compound XIVc used therein of an equimolar quantity of l-XIVk produced l-XVk hydrochloride; m.p. 265°–267° C.

Anal. Calc'd. for $C_{19}H_{25}NO_2.HCl$: C, 67.94; H, 7.80; N, 4.17. Found: C, 67.99; H, 7.81; N, 4.14. $[\alpha]_D^{25}$ = +55.5° (C, 0.0279; methanol).

The overall yield of l-XVk from compound XVIa was 12%.

We claim:

1. A compound having the formula

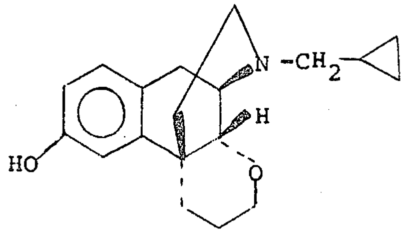

or a pharmaceutically acceptable acid addition salt thereof.

2. The hydrochloride salt of the compound of claim 1.

3. A tartrate salt of the compound of claim 1.

4. The levorotatory isomer of the compound of claim 1.

5. The dextrorotatory isomer of the compound of claim 1.

* * * * *